United States Patent
Scribben et al.

(10) Patent No.: US 10,493,205 B2
(45) Date of Patent: Dec. 3, 2019

(54) PROCESSES FOR DELIVERY OF VISCOUS DRUG THERAPIES

(71) Applicant: Battelle Memorial Institute, Columbus, OH (US)

(72) Inventors: Eric C. Scribben, Springfield, OH (US); Steven M. Risser, Reynoldsburg, OH (US); Amy M. Heintz, Dublin, OH (US); Jeffrey L. Ellis, Gahanna, OH (US); John D. Clay, Gahanna, OH (US); Timothy M. Blum, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 9 days.

(21) Appl. No.: 15/652,214

(22) Filed: Jul. 17, 2017

(65) Prior Publication Data

US 2017/0312434 A1   Nov. 2, 2017

Related U.S. Application Data

(62) Division of application No. 14/356,859, filed as application No. PCT/US2012/063852 on Nov. 7, 2012, now Pat. No. 9,737,662.

(Continued)

(51) Int. Cl.
*A61M 5/20* (2006.01)
*A61M 5/19* (2006.01)
(Continued)

(52) U.S. Cl.
CPC ............... *A61M 5/20* (2013.01); *A61M 5/19* (2013.01); *A61M 5/284* (2013.01); *A61M 5/286* (2013.01);
(Continued)

(58) Field of Classification Search
CPC .... A61M 5/19; A61M 5/284; A61M 5/31596; A61M 2202/07; A61M 5/2448;
(Continued)

(56) References Cited

U.S. PATENT DOCUMENTS

| 4,655,747 A | 4/1987 | Allen, Jr. |
| 5,045,065 A | 9/1991 | Raulerson |

(Continued)

FOREIGN PATENT DOCUMENTS

WO   2010056657 A2   10/2010

OTHER PUBLICATIONS

"Viscosity", (Mar. 4, 2013). MyChemE. Retrieved Apr. 7, 2016, from http://www.mycheme.com/viscosity/ (Year: 2013).*

(Continued)

*Primary Examiner* — Nilay J Shah
(74) *Attorney, Agent, or Firm* — Frank Rosenberg

(57) ABSTRACT

Core annular flow is used to enable the subcutaneous delivery of a viscous fluid such as a protein therapeutic formulation. The high-viscosity fluid is surrounded by a low-viscosity fluid, and the low-viscosity fluid lubricates the passage of the high-viscosity fluid. This allows the use of protein formulations that have a higher concentration and a higher viscosity at comparatively reduced injection forces and reduced injection times. Several different embodiments of injection devices that provide core annular flow are described herein.

10 Claims, 33 Drawing Sheets

Related U.S. Application Data

(60) Provisional application No. 61/556,491, filed on Nov. 7, 2011, provisional application No. 61/673,864, filed on Jul. 20, 2012.

(51) Int. Cl.
  *A61M 5/28* (2006.01)
  *A61M 5/24* (2006.01)
  *A61M 5/31* (2006.01)
  *A61M 5/315* (2006.01)

(52) U.S. Cl.
  CPC ............ *A61M 5/204* (2013.01); *A61M 5/2448* (2013.01); *A61M 5/3134* (2013.01); *A61M 5/31596* (2013.01); *A61M 2005/247* (2013.01); *A61M 2005/3128* (2013.01); *A61M 2005/31598* (2013.01); *A61M 2202/07* (2013.01); *A61M 2206/18* (2013.01)

(58) Field of Classification Search
  CPC ............ A61M 2206/18; A61M 5/3134; A61M 5/31598; A61M 2005/3201; A61M 5/007; A61M 5/24
  See application file for complete search history.

(56) References Cited

U.S. PATENT DOCUMENTS

| | | |
|---|---|---|
| 5,114,240 A | 5/1992 | Kindt-Larsen et al. |
| 5,429,603 A | 7/1995 | Morris |
| 6,692,468 B1 | 2/2004 | Waldenburg |
| 7,666,413 B2 | 2/2010 | Liu et al. |
| 9,056,200 B2 | 6/2015 | Uber et al. |
| 2006/0280690 A1* | 12/2006 | Wright ............ A61B 17/00008 424/45 |
| 2009/0036869 A1 | 2/2009 | Abuzaina |
| 2010/0217231 A1* | 8/2010 | Ilan ................. A61B 17/00491 604/506 |
| 2010/0228121 A1 | 9/2010 | Kazuhiro et al. |

OTHER PUBLICATIONS

International Search Report from PCT/US2012/063852 dated Mar. 2, 2013.
International Preliminary Examination Report from PCT/US2012/063852 dated May 13, 2014.
Written Opinion of the International Searching Authority from PCT/US2012/063852 dated Mar. 15, 2013.
Official Action from EP Application No. 12848049.8 dated Jun. 16, 2017.

\* cited by examiner

PROCESSES FOR DELIVERY OF VISCOUS DRUG THERAPIES

CROSS-REFERENCE TO RELATED APPLICATIONS

This application is a divisional of U.S. patent application Ser. No. 14/356,859 filed May 5, 2014, now U.S. Pat. No. 9,737,662 which was a national stage filing claiming the priority benefit of PCT/US2012/063852 filed Nov. 7, 2012 and also claims priority to U.S. Provisional Patent Application Ser. No. 61/556,491, filed on Nov. 7, 2011, and to U.S. Provisional Patent Application Ser. No. 61/673,864, filed on Jul. 20, 2012. The entireties of those disclosures are fully incorporated by reference herein.

BACKGROUND

The present disclosure relates to injection devices, compositions and processes for delivering viscous fluids, such as pharmaceutical protein formulations, to a patient using core annular flow. This reduces the injection force needed to deliver the fluid, and can reduce the amount of fluid without changing the amount of delivered therapy.

Protein therapeutics is an emerging class of drug therapy that promises to provide treatment for a broad range of diseases, such as autoimmune disorders, cardiovascular diseases, and cancer. The dominant delivery method for protein therapeutics, particularly monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics by injection is also complicated by the high molecular weight of such proteins. The high molecular weight results in a high viscosity for the therapeutic formulation. For example, many monoclonal antibody formulations would be delivered in concentrations greater than 150 mg/mL when injection is used, and this results in the formulation having an absolute viscosity exceeding 5 centipoise (cP). The dosages required for some therapeutic proteins can necessitate a protein concentration in the range of 150 to 500 mg/mL or higher. These concentrations can have absolute viscosities exceeding 50 cP, making them unsuitable for delivery by conventional injection devices.

Some methods have been considered to improve protein delivery via injection. For example, U.S. Pat. No. 7,666,413 describes a method of reducing the viscosity of high concentration protein formulations by adding a salt that increases the ionic strength of the formulation, thereby decreasing self-association between protein molecules. However, this method only extends the usable concentration range of the formulation to about 100 mg/mL, at which point the viscosity still exceeds 20 cP. Estimates of the injection force required to inject a 20 cP formulation through a common 27 gauge needle with a syringe in 10 to 20 seconds is approximately 40 N or 20 N, respectively, which is higher than suitable for most injection devices. Furthermore, higher concentration protein formulations are unstable and will aggregate over time, losing their activity.

PCT Publication No. WO2010/056657 discloses the use of protein suspensions to achieve low viscosity, high concentration protein formulations of up to 200 mg/mL. An insoluble protein particle is suspended in a non-solvent; depending on the non-solvent, viscosity as low as 3 cP is claimed. However, this approach requires identifying a non-solvent that is safe for injection and does not cause pain. In addition, the stability of the protein in contact with the non-solvent is not demonstrated.

The interior of the syringe barrel and the exterior of the plunger are commonly lubricated with silicone oil (in a layer having a thickness of approximately 100 nanometers) to reduce the friction at the interface of the two parts. This approach may reduce the gliding force and/or injection force associated with boundary layer fluid flow within the barrel. In addition, the silicone oil can migrate from the barrel surface into the solution being injected, which could adversely influence the stability and activity of the protein in the protein therapeutic formulation. Other coating technologies have been developed more recently, such as Tribo-Glide®, from Tribo Film Research, Inc. and IVEK Corporation, which provides more effective friction reduction. The major pressure source however is fluid flow through the needle, and these lubricants do not address that issue. Thus, substantial force is still required to inject high-viscosity solutions.

It would be desirable to provide processes and devices by which a high-viscosity fluid could be administered through a conventional syringe with reduced injection force in a reasonable injection time. These could be used to deliver high-concentration protein, or other high viscosity pharmaceutical formulations.

BRIEF DESCRIPTION

Devices, compositions, and processes to enable subcutaneous delivery of viscous fluids with reduced injection force using available volumes and injection times are described herein. Briefly, core annular flow is used to deliver such viscous fluids. Highly viscous fluid is located in the "core" and is lubricated by a lower viscosity fluid which forms an annulus around the highly viscous fluid. This significantly reduces the amount of force required for injection, and can enable the use of current injection technologies for the delivery of highly viscous fluids as well as enabling the development of new delivery strategies. The injection devices described herein can be used to deliver a high-viscosity fluid to a patient.

Disclosed in some embodiments is an injection device for delivering a high-viscosity fluid, comprising: a barrel and a plunger operating within the barrel. The barrel has an interior space for containing the high-viscosity fluid to be, dispensed by the injection device, the interior space being formed by a sidewall. The barrel also has an open end and a closed plunger end, and the open end includes a nozzle having a constriction point and an orifice. The barrel also includes an inner concentric wall within the sidewall, an opening being positioned between a bottom edge of the inner concentric wall and the nozzle. The inner concentric wall defines an inner compartment having the high-viscosity fluid and an outer compartment having a low-viscosity fluid within the barrel. The inner concentric wall has one or more openings permitting fluid communication between the inner and outer compartments. The plunger is adapted to provide a depressing force substantially concurrently to a high-viscosity fluid within the inner compartment and a low-viscosity fluid within the outer compartment, thereby producing an annulus of the low-viscosity fluid around a core of the high-viscosity fluid as the fluids are dispensed from the orifice.

The ratio of the viscosity of the high-viscosity fluid to the viscosity of the low-viscosity fluid may be from about 60 to about 200. In other embodiments, the ratio of a cross-sectional area of the inner compartment to a cross-sectional area of the outer compartment is from about 2:1 to about 9:1. Sometimes, the nozzle tapers from the constriction point to the orifice.

The injection device may further comprise a means for sealing located at the constriction point which ruptures when the plunger is depressed. The means for sealing may be located across only the inner concentric wall.

In some embodiments, a valve mechanism is located at the bottom edge of the inner concentric wall. In other embodiments, the inner concentric wall includes a lower wall that tapers to form an aperture, and a means for sealing is located at the aperture. The injection device can sometimes further comprise a wire extending longitudinally at the aperture. The injection device may also further comprise grooves at the open end of the barrel.

Disclosed in other embodiments is an injection device for delivering a high-viscosity fluid, comprising a barrel having an interior space formed from a sidewall, an open end, and a closed plunger end. The open end has an orifice. The barrel also has a rupturable sealing membrane that separates the interior space of the barrel into an upper compartment and a lower compartment. The high-viscosity fluid is located in the upper compartment, and a low-viscosity fluid is located in the lower compartment. A plunger can move within the barrel. Depressing the plunger produces an annulus of the low-viscosity fluid around a core of the high-viscosity fluid as the fluids are dispensed from the orifice.

Disclosed in other embodiments is an injection device for delivering a high-viscosity fluid, comprising a barrel having an interior space formed from a sidewall, an open end, and a closed plunger end. The open end has an orifice. The barrel also has a radial wall that separates the interior space of the barrel into an upper compartment and a lower compartment. The radial wall includes an aperture aligned with the orifice in the open end of the barrel, the aperture being sealed with a sealing means. The high-viscosity fluid is located in the upper compartment, and a low-viscosity fluid is located in the lower compartment. A plunger can move within the barrel. Depressing the plunger produces a pressure which pushes the high-viscosity fluid through the aperture and produces an annulus of the low-viscosity fluid around a core of the high-viscosity fluid as the fluids are dispensed from the orifice.

The injection device may further comprise grooves at the open end of the barrel to promote core annular flow.

In yet other embodiments disclosed herein, an injection device for delivering a high-viscosity fluid is described that comprises: a barrel and a plunger. having an open end and a closed end; and a plunger operating within the barrel. The barrel has an interior space formed from a sidewall, an open end, and a closed plunger end. The open end has an orifice. The interior space of the barrel contains one or more beads, wherein each bead includes a core and a shell, the high-viscosity fluid being located in the core. Depressing the plunger produces an annulus of low-viscosity fluid around a core of the high-viscosity fluid as the fluids are dispensed from the orifice.

In some embodiments, the interior space of the barrel further includes the low-viscosity fluid. The shell is a biocompatible polymer which is insoluble in the low-viscosity fluid, and the injection device further includes a means for breaking the shell. In other embodiments, the shell is soluble in the low-viscosity fluid.

In some different embodiments, the injection device further comprises an inlet at the open end and a fluid reservoir connected to the barrel through the inlet, the low-viscosity fluid being located within the fluid reservoir; and the bead is shaped to create an annulus within the barrel. This injection device may further comprise a sealing means within the inlet. Withdrawing the plunger from the barrel causes the low-viscosity fluid to enter the interior space of the barrel and interact with the bead(s). In other embodiments, this injection device may further comprise an outlet at the closed end and an outlet reservoir connected to the barrel through the outlet. Excess low-viscosity fluid can enter the outlet reservoir as the plunger is withdrawn beyond the outlet. The injection device can be generally stored with the plunger partially depressed into the barrel.

The injection device may further comprise a sonic generator located at the open end of the barrel, or may further comprise grooves at the open end of the barrel, both of which can be used to promote core annular flow.

Also disclosed in various embodiments is an injection device, comprising: a barrel having an open end and a closed end; a plunger operating within the barrel; and an inlet at the open end and a fluid reservoir connected to the barrel through the inlet.

This injection device may further comprise a sealing means within the inlet. In other embodiments, this injection device may further comprise an outlet at the closed end and an outlet reservoir connected to the barrel through the outlet. This injection device may also further comprise a bead within the barrel, the bead being shaped to create an annulus within the barrel, wherein the bead includes a core and a shell, the high-viscosity fluid being located in the core and the shell surrounding the high-viscosity fluid. The injection device may further comprise grooves at the open end of the barrel.

Also disclosed in various embodiments herein is an injection device for delivering a high-viscosity fluid, comprising: a barrel having an interior space formed from a sidewall, an open end, and a closed plunger end, the interior space containing a low-viscosity fluid and a high-viscosity fluid, and the open end having an orifice; a plunger movably operable within the barrel; and a sonic generator located at the open end of the barrel for producing an annulus of the low-viscosity fluid around a core of the high-viscosity fluid as the fluids are dispensed from the orifice. If desired, the injection device may further comprise grooves at the open end of the barrel.

The present disclosure also relates in various embodiments to an injection device for delivering a high-viscosity fluid, comprising: a barrel having an open end and a closed end, the open end having an orifice; and a plunger operating within the barrel; wherein the barrel is formed from a sidewall, and the sidewall includes grooves at the open end. When the barrel contains a low-viscosity fluid and a high-viscosity fluid, the grooves can be used to produce an annulus of the low-viscosity fluid around a core of the high-viscosity fluid as the fluids are dispensed from the orifice.

The sidewall may taper at the open end to an orifice. Sometimes, the injection device further comprises an inner wall within the barrel that separates the barrel into a first compartment and a second compartment. The injection device can alternatively further comprise a sealing means at a bottom edge of the inner wall.

Also disclosed herein is an injection device for creating core annular flow, comprising: a barrel; a plunger operating within the barrel; and a flow diverter. The barrel has an interior space formed from a sidewall, an open end having an orifice, and an inner concentric wall within the sidewall. The inner concentric wall divides the interior space into an inner compartment and an outer compartment. The flow diverter is located between the inner compartment and an orifice. The flow diverter is adapted so that fluid flows from the inner compartment to an annulus of the barrel and so that fluid flows from the outer compartment as a core.

In some embodiments, the flow diverter can be formed from a flow cap and a flow base. A center of the flow cap connects to the inner concentric wall. At least one radial spoke extends from the center of the flow cap to an annular ring. An underside of the annular ring includes a circumferential groove, the circumferential groove creating an inner ring wall and an outer ring wall. The flow base includes a central surface with at least one radial spoke extending from the central surface to an annular wall. The at least one radial spoke of the flow cap and the at least one radial spoke of the flow base cooperate to form a tunnel that channels fluid from the inner compartment to the circumferential groove. The central surface of the flow base may have a diameter equal to an outer diameter of the inner concentric wall. The annular wall of the flow base may have an outer diameter equal to the outer diameter of the inner ring wall of the flow cap. The inner concentric wall and the flow cap can be formed as one integral component or as two separate components. The flow cap may include throughbores between the inner concentric wall and the inner ring wall; and the flow base may include throughbores between the central surface and the annular wall. In some embodiments, the flow cap may rest upon a horizontal stop surface within a needle hub, and the flow base may be seated within the needle hub.

The plunger may comprise a central piston located within the inner compartment and a ring piston located within the outer compartment, the central piston and the ring piston being connected to a common shaft.

Also disclosed herein is an injection device for creating core annular flow, comprising: a barrel formed by a sidewall and having a lower volume and an upper volume; a core container located within the lower volume, the core container comprising a sidewall and a floor with a central hole; a plunger rod extending through the barrel upper volume and contacting a core plunger in the core container; a needle hub at an end of the barrel opposite the plunger rod, the needle hub having an internal passage and an annular passage; and a hollow pin having at least one side port at an upper tip, the at least one side port being covered by the floor of the core container, the hollow pin regulating flow from the core container to the internal passage of the needle hub; wherein an annular compartment is formed between the sidewall, the core container, the plunger rod, and the needle hub. High-viscosity fluid can flow from the core container through the hollow pin and the internal passage, and wherein low-viscosity fluid can flow from the annular compartment through the annular passage.

The core plunger and the plunger rod may be connected to each other. The core plunger may cooperate with at least one groove at a top of the core container sidewall. The upper volume of the barrel may have a smaller diameter than the lower volume of the barrel. The core container may divide the lower volume into an upper space, a lower space, and a lower annular space fluidly connecting the upper space and the lower space. The needle hub may comprise an internal surface upon which the hollow pin sits, the internal surface having a central hole that communicates with the internal passage and at least one slit spaced apart from the central hole that communicates with the annular passage. A base of the hollow pin may include a radial flange. The internal passage and the annular passage of the needle hub may bee separated by an internal cylindrical wall.

Also disclosed herein in different embodiments is an injection device for delivering a high-viscosity pharmaceutical formulation, comprising: a barrel; a needle attached to an orifice in the barrel; and a plunger operating within the barrel. An interior surface of the needle is coated with a low-viscosity fluid surrounding the high-viscosity fluid such that the high-viscosity fluid does not contact the needle. The low-viscosity fluid may be a phase change material.

Also disclosed herein is an injection device for delivering a high-viscosity pharmaceutical formulation, comprising: a hollow barrel having an orifice; and a plunger operating within the barrel. The barrel includes a first compartment, a second compartment, and at least one channel connecting the second compartment to the first compartment, the channel being shaped so that fluid flows from the second compartment circumferentially against a sidewall of the first compartment to create core annular flow. The first compartment contains the high-viscosity formulation. The second compartment contains a low-viscosity fluid.

In some embodiments, the barrel is an outer barrel containing the first compartment, and the device further comprises an inner barrel that slides within the outer barrel, the inner barrel containing the second compartment.

Alternatively, the barrel may include an inner wall that divides an interior space of the barrel into the first compartment and the second compartment, the orifice being located within the first compartment.

Also disclosed herein in various embodiments is a process for delivering a high-viscosity pharmaceutical formulation, comprising: receiving the high-viscosity pharmaceutical formulation in an injection device barrel; and injecting the pharmaceutical formulation into a patient, wherein a low-viscosity fluid forms an annulus about the high-viscosity formulation as the pharmaceutical formulation is injected.

The low-viscosity fluid may comprise water, a water based solution, saline, a perfluoroalkane solvent, safflower oil, or benzyl benzoate. A ratio of the viscosity of the high-viscosity formulation to the viscosity of the low-viscosity fluid may be from about 60 to about 200. A fraction of the width of the injection device barrel occupied by the high-viscosity formulation may be from about 0.70 to less than 1. The high-viscosity formulation can have an absolute viscosity of from about 5 centipoise to about 1000 centipoise.

In some embodiments, the high-viscosity formulation contains a protein having a concentration of from about 150 mg/mL to about 500 mg/mL. In other embodiments, a velocity gradient of the low-viscosity fluid is greater than a velocity gradient of the high-viscosity formulation during injection.

Sometimes, the pharmaceutical formulation is injected with a pressure of 20 Newtons or less. Other times, the pharmaceutical formulation is injected within an injection time of 30 seconds or less.

The low-viscosity fluid may be stored in a different compartment from the high-viscosity formulation, and the low-viscosity fluid flows circumferentially about the high-viscosity formulation during the injecting.

These and other non-limiting aspects and/or objects of the disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 8 is a diagram showing a Y-shaped apparatus used to simulate core annular flow.

FIG. 9 is a graph showing the pressure drop vs. flow rate for different solutions, some with core annular flow (open symbols) and some without core annular flow (filled symbols).

FIG. 10 is an illustration of an injection device having a concentric wall that separates the barrel into two compartments. An opening at the bottom of the concentric wall permits the fluids in the two compartments to achieve core annular flow.

FIG. 11 is a variation on the injection device of FIG. 10, with a nozzle or tapered end.

FIG. 12 is a top view of the closed end of the injection device of FIG. 10 and FIG. 11, where the plunger is inserted, showing how inner walls within the barrel are supported.

FIG. 13 is a variation on the injection device of FIG. 10, having a valve mechanism for the inner compartment to release high-viscosity fluid in the form of drops that are surrounded by low-viscosity fluid.

FIG. 14 is a variation on the injection device of FIG. 10, with the inner wall tapered and including a sealing means at the bottom. This embodiment acts as a "syringe within a syringe".

FIG. 15 is an illustration of an injection device having a sealing membrane that separates the barrel into an upper compartment and a lower compartment. The lower compartment contains an expandable pouch containing low-viscosity fluid.

FIG. 16 is an illustration of an injection device in which the high-viscosity fluid is in the core of a bead and is surrounded by a shell that separates it from the low-viscosity fluid.

FIG. 17 is an illustration of an injection device in which the high-viscosity fluid is in the form of a core/shell bead stored in the barrel. The low-viscosity fluid is stored in a fluid reservoir outside the barrel and is drawn into the barrel during usage. If desired, an outlet reservoir may also be present.

FIG. 18 is an illustration of an injection device having a sonic generator at the base.

FIG. 19 is an illustration of an injection device having a floor that separates the barrel into an upper compartment and a lower compartment. An aperture in the floor is aligned with the orifice leading to the needle.

FIG. 20 is an illustration of the injection device of FIG. 19 being injected. The high-viscosity fluid from the upper compartment shoots at high speed through the lower compartment, drawing low-viscosity fluid along with it to create core annular flow.

FIG. 21 is a perspective illustration of an injection device having grooves in the sidewall leading to the needle to encourage low-viscosity fluid to remain along the wall and high-viscosity fluid to remain in the core.

FIG. 22 is a top view of the closed end of an injection device showing a first possible construction for an inner wall.

FIG. 23 is a top view of the closed end of an injection device showing a second possible construction for an inner wall.

FIG. 24 is a top view of the closed end of an injection device showing a third possible construction for an inner wall.

FIG. 25 is an illustration of an experimental setup for an injection device having core annular flow.

FIG. 26 is a magnified view of the test cell of the setup of FIG. 25 showing the portion that induces core annular flow.

FIG. 27 is a perspective interior view of an exemplary embodiment of an injection device that uses flow inversion.

FIG. 28 is a perspective view of some internal components of the injection device.

FIG. 29 is a bottom view of a flow cap of the injection device.

FIG. 30 is a perspective view of a flow base of the injection device.

FIG. 31 is a perspective view of a needle hub of the injection device.

FIG. 32 is a side cross-sectional view of the injection device showing fluid flow.

FIG. 33 is a perspective view of the internal components of another exemplary embodiment of a "stacked" injection device.

FIG. 34 is a side view of the internal components of the injection device.

Figure 35:
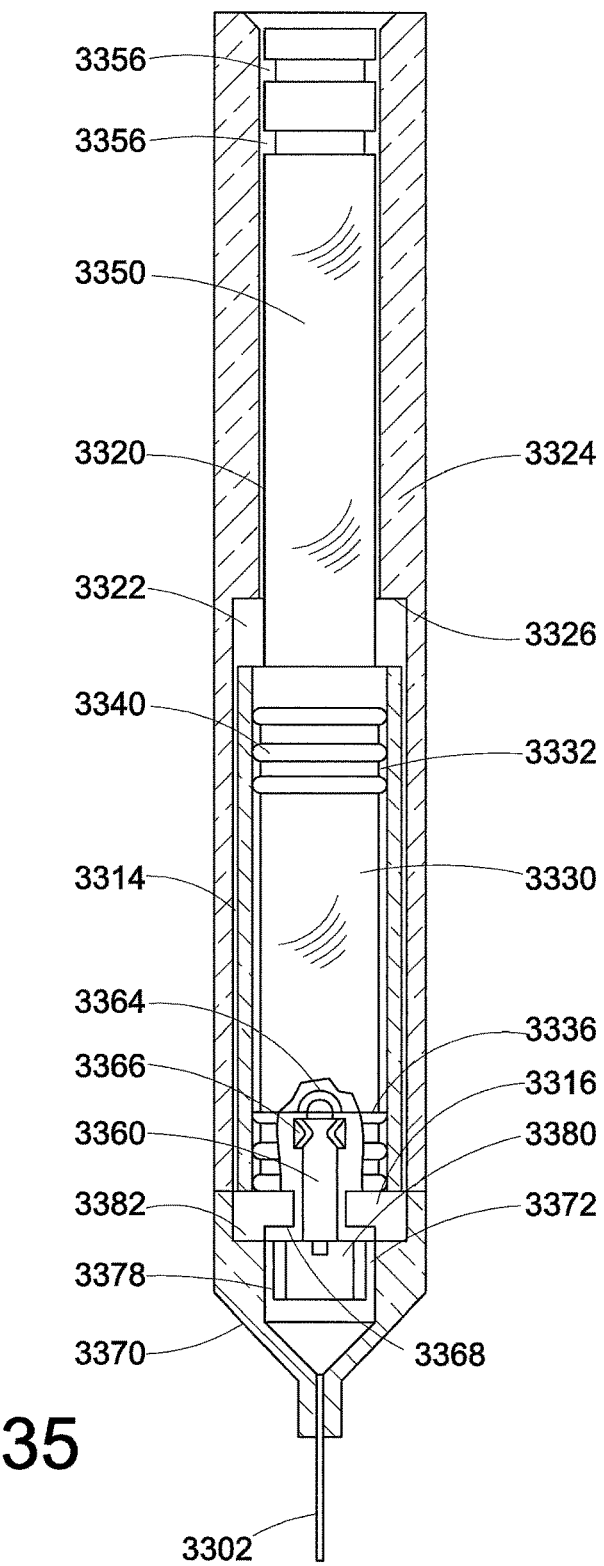

FIG. 35 is a side cross-sectional view of the internal components of the injection device.

Figure 36:
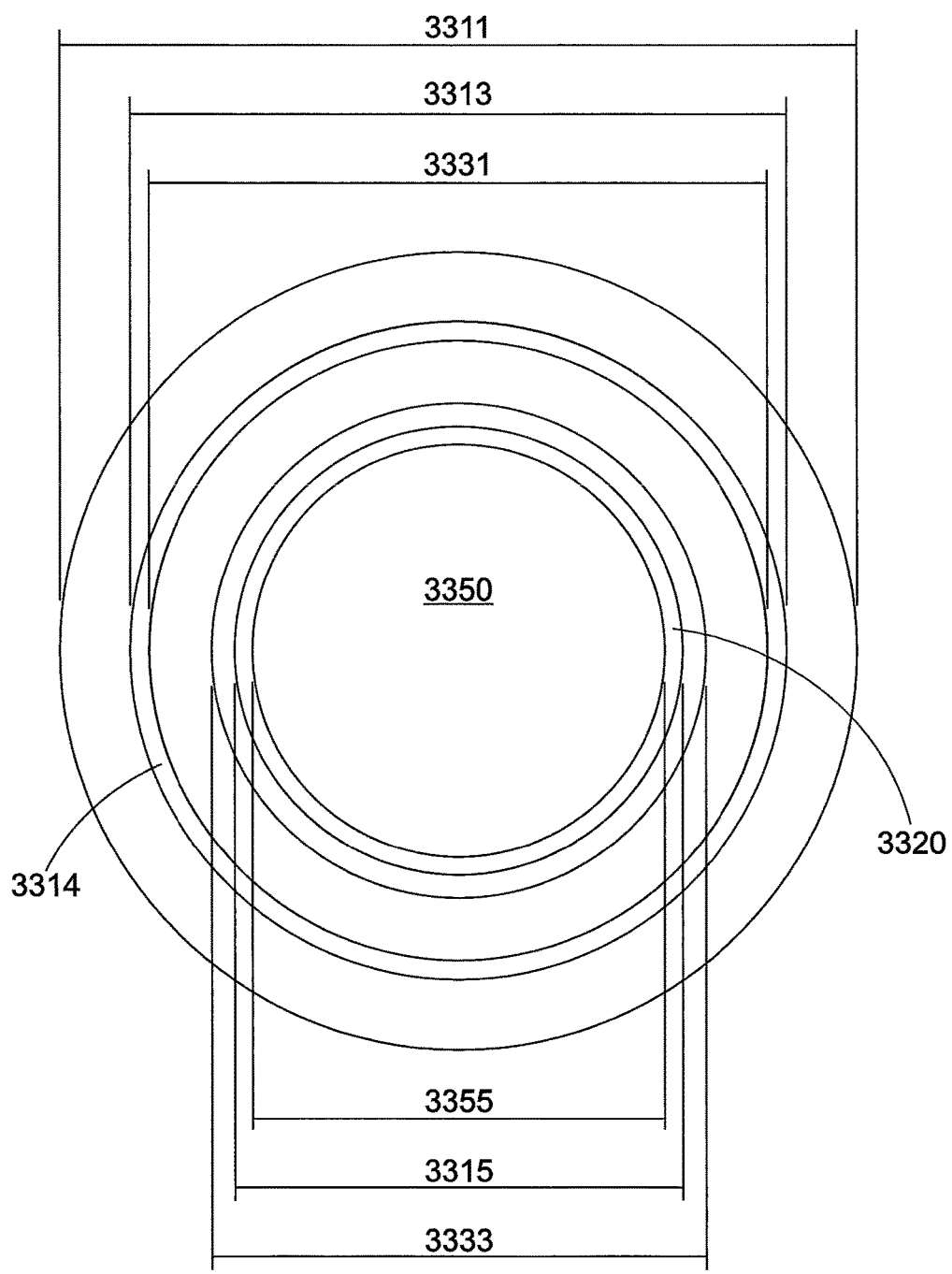

FIG. 36 is a plan cross-sectional view showing the diameters of various internal components of the injection device.

Figure 37:
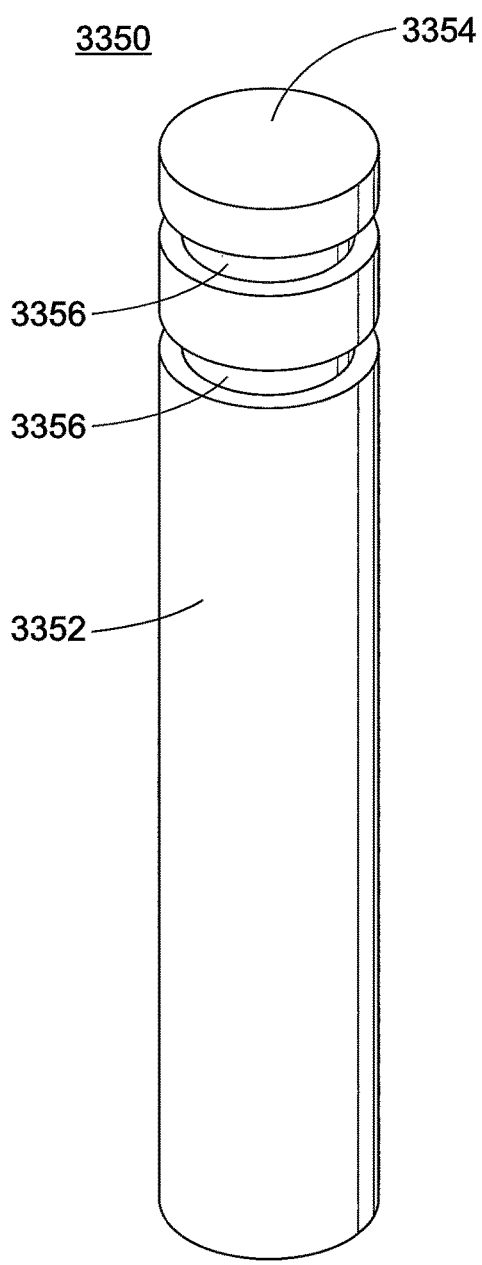

FIG. 37 is a view of the plunger rod of the injection device.

Figure 38:
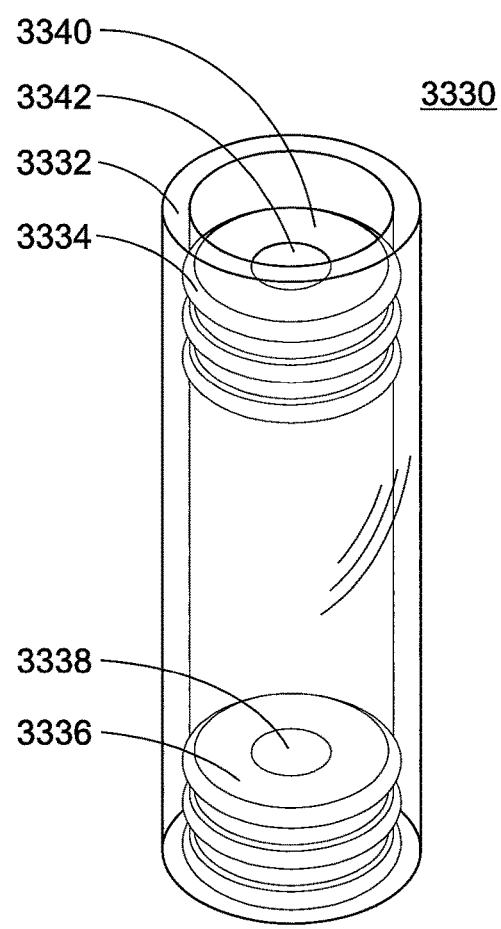

FIG. 38 is a view of the core container of the injection device.

Figure 39:
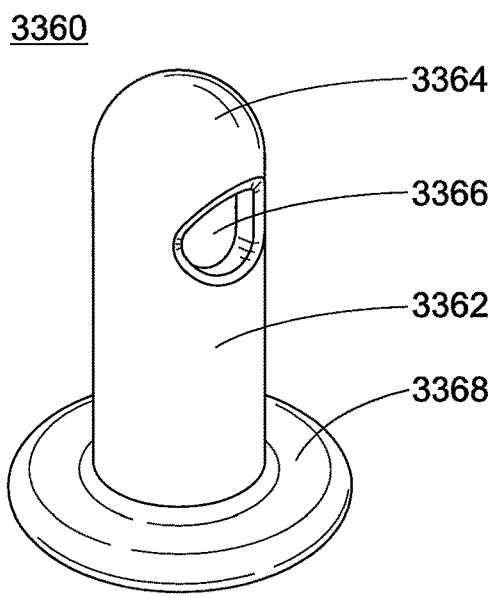

FIG. 39 is a view of the hollow pin which is located within the base of the injection device.

Figure 40:
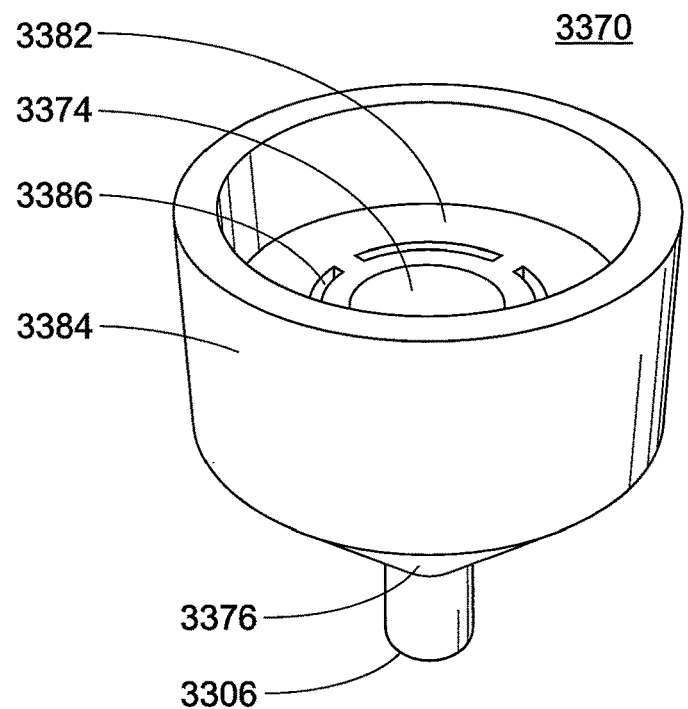

FIG. 40 is a perspective view of the needle hub.

DETAILED DESCRIPTION

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the following specification and the claims which follow, reference will be made to a number of terms which shall be defined to have the following meanings.

The singular forms "a," "an," and "the" include plural referents unless the context clearly dictates otherwise.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

The term "room temperature" refers to a temperature from 23° C. to 25° C.

Viscosity can be defined in two ways: "kinematic viscosity" or "absolute viscosity." Kinematic viscosity is a measure of the resistive flow of a fluid under an applied force. The SI unit of kinematic viscosity is mm$^2$/sec, which is 1 centistoke (cSt). Absolute viscosity, sometimes called dynamic or simple viscosity, is the product of kinematic viscosity and fluid density. The SI unit of absolute viscosity is the millipascal-second (mPa-sec) or centipoise (cP), where 1 cP=1 mPa-sec.

A "protein" is a sequence of amino acids that is of sufficient chain length to produce a tertiary or quaternary structure. Examples of proteins include monoclonal antibodies, insulin, human growth hormone, and erythropoietin.

The present disclosure discloses processes for achieving low injection force with high-concentration protein solutions and maintaining the protein stability and activity. The phenomenon of core annular flow (CAF) is used to reduce the pressure required to deliver a given volumetric flow rate. Generally, a highly viscous fluid is delivered in the core of a flow field along with a lower viscosity fluid in an annular region (i.e. between the core and the walls of the delivery system) to lubricate flow and reduce the pressure required relative to non-lubricated flow. The processes of the present disclosure can be used with both manual syringes or auto-injectors and is not limited to cylindrical geometries. For the purposes of this disclosure, the term "injection device" is used to refer to both manual syringes and auto-injectors of any size or shape.

Figure 1:
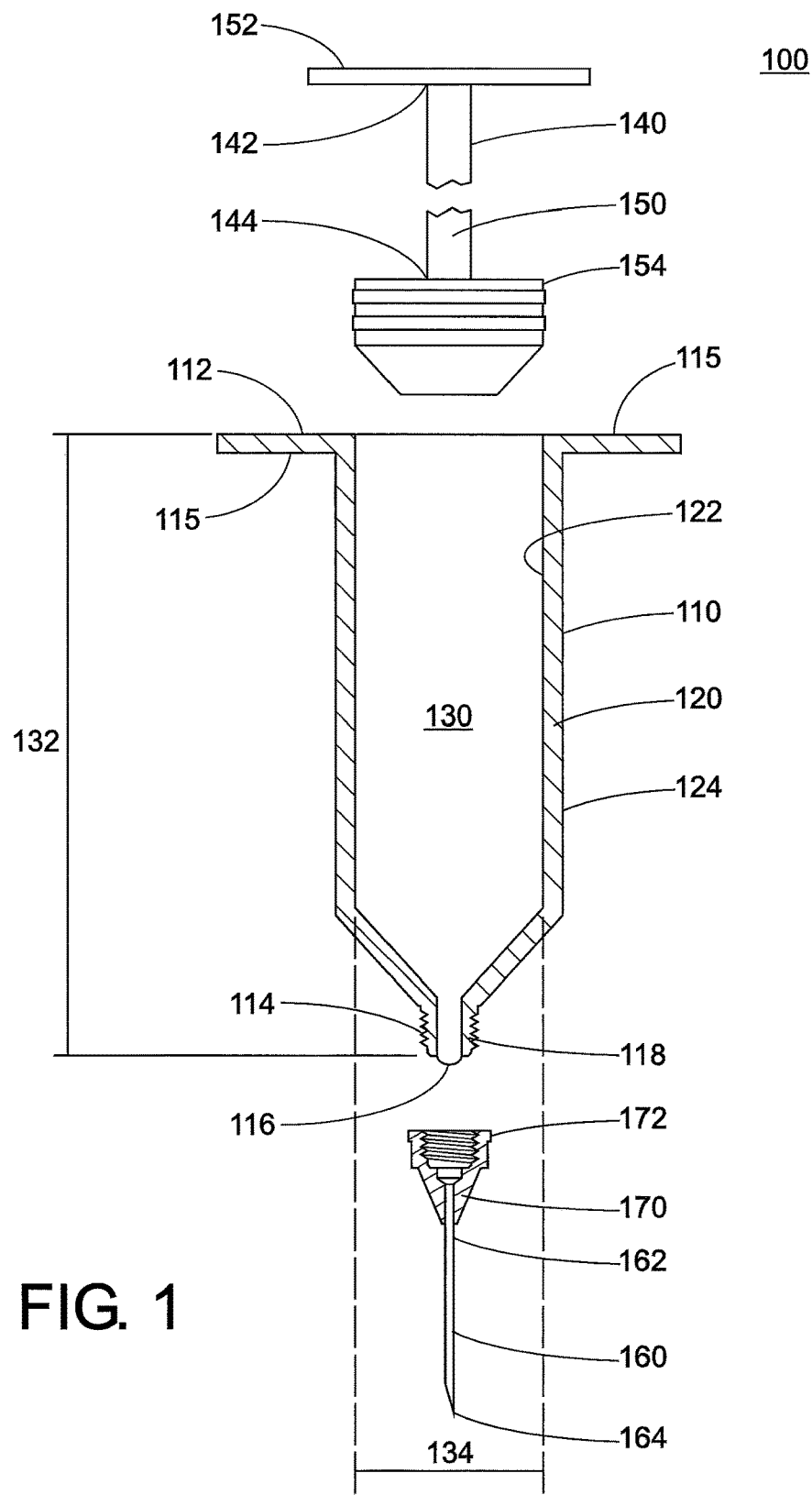
FIG. 1 is a diagram showing the various components of a conventional hypodermic syringe.

FIG. 1 is a diagram showing the various components of a conventional hypodermic syringe 100. The syringe includes a barrel 110, a plunger 140, and a needle 160.

The barrel 110 is the part of the hypodermic syringe that contains the fluid to be injected into a patient. The barrel 110 is hollow and has a plunger end 112 and a needle end 114. The plunger end may also be referred to as a closed end 112 of the barrel, because fluid will not pass through this end when the plunger 140 is inserted. Similarly, the needle end may also be referred to as an open end 114 of the barrel because fluid can pass through this end when the needle 160 is attached. The barrel is formed from a sidewall 120 that surrounds an interior space 130. The sidewall 120 includes an interior surface 122 and an exterior surface 124. The barrel itself is usually transparent for viewing of fluid within the interior space, and a scale can also be imprinted on the exterior surface. The needle end 114 can be tapered towards an orifice 116 through which fluid exits the interior space 130. The length 132 and width 134 of the barrel is variable, as is its shape, although generally the barrel is cylindrical. In this regard, the diameter of the barrel corresponds to the width 134 when the barrel is cylindrical. The needle end 114 also includes a female fitting 118 to form a leak-free connection with the needle 160. The plunger end 112 also includes a finger flange 115 which flares out from the barrel, and allows the user to press on the plunger 140 with the thumb while holding the barrel in place with two fingers.

The plunger 140 is used to discharge fluid present in the barrel 110 of the syringe. The plunger 140 includes a shaft 150 with a thumbrest 152 on one end 142 and a stopper or piston 154 on the other end 144. The shaft is long enough for the stopper 154 to travel the length of the interior space 130 of the barrel. The stopper 154 fits snugly against the interior surface 122 of the barrel to make an airtight seal. As previously mentioned, a lubricant (not visible) is typically present between the stopper 154 and the interior surface 122 of the barrel to reduce the gliding force.

The needle 160 is essentially a small thin tube, and is part of the syringe that actually pierces the skin of the patient. On one end 162 is a hub 170, which includes a male fitting 172 for attachment to the needle end of the barrel, such as a Luer lock. The other end of the needle is beveled 164 to increase the ease of insertion into the patient.

Figure 2:
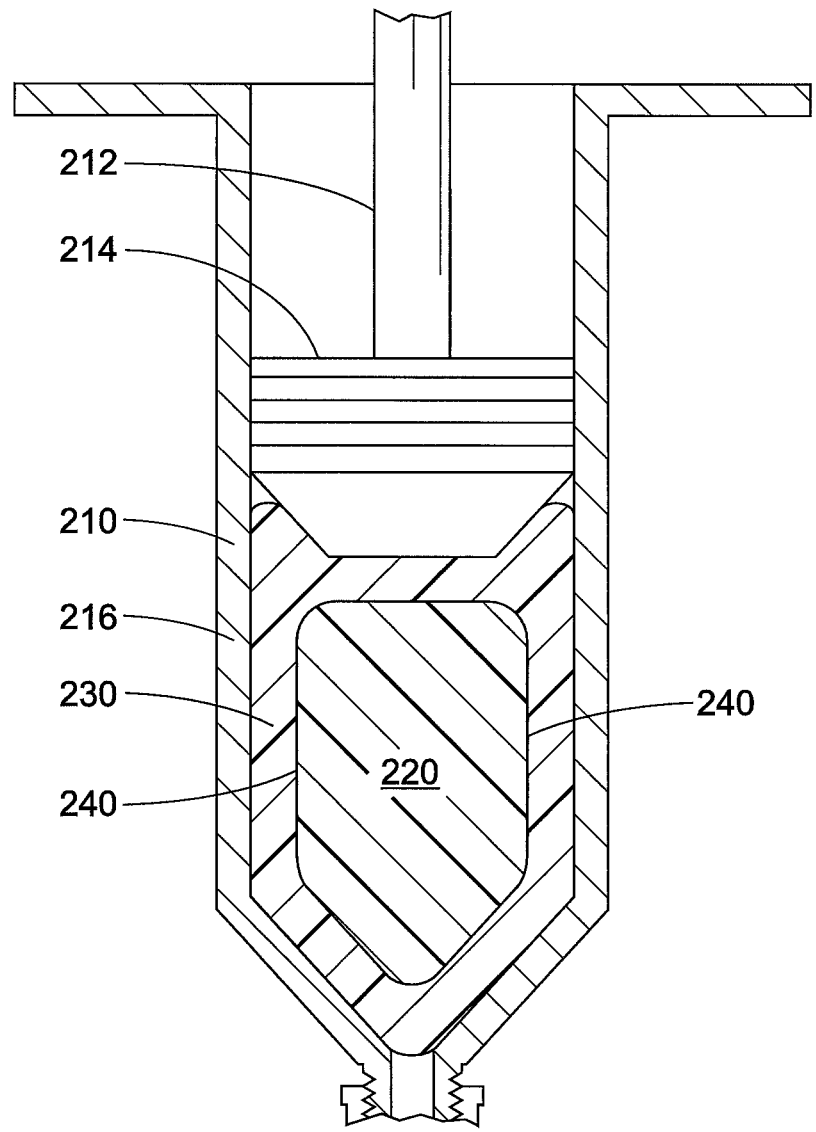
FIG. 2 is a diagram showing an exemplary embodiment of an injection device containing a high-viscosity fluid and a low-viscosity fluid for injection.

In the processes of the present disclosure, core annular flow is used to reduce the pressure needed to dispense a viscous fluid from an injection device. FIG. 2 shows an illustrative embodiment of one means for obtaining core annular flow. This figure shows an injection device barrel 210 with the plunger 212 inserted and the stopper 214 visible. Located in the interior space of the barrel is a high-viscosity pharmaceutical formulation 220 which is surrounded by a low-viscosity fluid 230. The high-viscosity formulation has a greater absolute viscosity than the low-viscosity fluid. The high-viscosity formulation here can be considered to have a core shape. The low-viscosity fluid, which surrounds the high-viscosity formulation, can be described as having an annular shape or forming an annulus around the high-viscosity formulation. The use of the term "annular" here does not exclude the low-viscosity fluid from being located above or below the core formed from the high-viscosity formulation. An interface region 240 exists in the longitudinal direction (along the axis of the injection device) where the low-viscosity fluid and the high-viscosity fluid meet.

It should be noted that the high-viscosity formulation 220 does not contact the sidewall 216 of the barrel. Only the low-viscosity fluid 230 contacts the sidewall 216. In other words, the low-viscosity fluid 230 is between the core 220 (formed by the high-viscosity fluid) and the walls 214 of the barrel. When the plunger is depressed, the low-viscosity fluid lubricates the flow and reduces the pressure required to eject the fluid from the barrel.

Generally, the low-viscosity annulus and high-viscosity core is produced during flow, and may not always be present within the structure. However, it is possible to create trapped high-viscosity core/low-viscosity annular structures through the use of phase change materials such as ice, thermally sensitive emulsions, etc.

The contents of the injection device can be arranged to obtain core annular flow by several methods. Some exemplary methods are depicted in the following figures.

In one method, the high-viscosity fluid and the low-viscosity fluid may be stored in two separate compartments, and then combined when the injection device is depressed. The core annular flow may be generated by directing the flow of the two fluids such that the low-viscosity fluid forms an annulus around the high-viscosity core. This may occur in the needle or within a section of the injection device barrel where the two compartments meet. Again, the injection device barrel need not be cylindrical. If an injection device barrel with an initial compartment containing a square cross section is used, the fluids could be injected on different sides a small distance apart, in order to create the core and annulus once the cylindrical section is reached.

Figure 3:
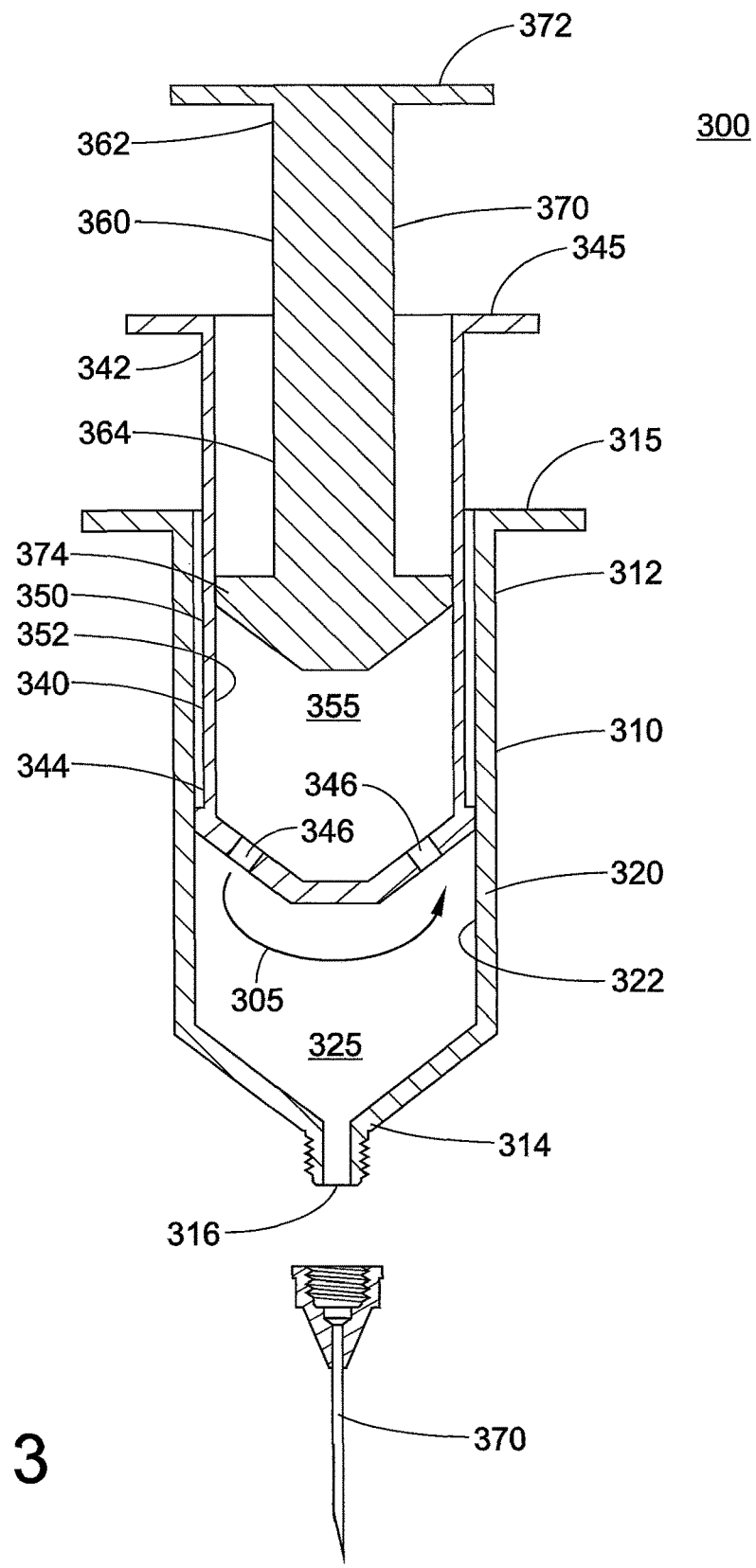
FIG. 3 is a diagram showing an injection device having two compartments, one for a high-viscosity fluid and one for a low-viscosity fluid. The compartments are made in the form of an inner barrel and an outer barrel.

An example of this method is depicted in FIG. 3. Syringes having two compartments are known in the art. Here, the injection device 300 contains two separate telescoping barrels. An outer barrel 310 is hollow and has a closed end 312 and an open end 314. The open end 314 may also be referred to as a needle end because a needle 302 is attached to this end, and fluid may exit the outer barrel 310 through the needle. The outer barrel 310 is formed from a sidewall 320 having an interior surface 322 and surrounding an interior space 325. The interior space of the outer barrel contains the high-viscosity fluid and can be considered a first compartment of the injection device. The open end 314 of the outer barrel includes an orifice 316 through which fluid exits the interior space/first compartment 325, and to which the needle is attached. The closed end of the outer barrel includes a first finger flange 315 that flares out radially from the outer barrel and provides one end of a grip for the user. Disposed within the outer barrel 310 is an inner barrel 340 which can slide within the outer barrel 310. The inner barrel is hollow, and has a plunger end 342 and a stopper end 344. The inner barrel is also formed from a sidewall 350 that surrounds an interior space 355. The interior space of the inner barrel contains the low-viscosity fluid and can be considered a second compartment of the injection device. The stopper end 344 forms an airtight seal with the outer barrel 310, and acts to push fluid contained in the interior space 325 of the outer barrel through the needle 302. The stopper end 344 notably contains one or more discrete channels 346 which permit fluid within the inner barrel 340 to be injected into the outer barrel 310. This channel flow is directed against the interior surface 322 of the outer barrel so that the low-viscosity fluid from the inner barrel travels circumferentially against the sidewall 320 and downwards towards the needle. The plunger end 342 of the inner barrel receives the plunger 360. The plunger end also includes a second finger flange 345 that flares out radially from the inner barrel. The plunger 360 itself includes a shaft 370 with a thumbrest 372 on one end 362 and a piston 374 on the other end 364. The piston 374 fits snugly against the interior surface 352 of the inner barrel 340 to make an airtight seal. The plunger 360 travels the length of the inner barrel as well.

In use, the plunger 360 is depressed to inject the low-viscosity fluid (not shown) from the interior space 355 of the inner barrel 340 into the interior space 325 of the outer barrel 310 and form an annulus about the high-viscosity fluid located in the outer barrel (indicated by circumferential arrow 305). It is believed that the inner barrel 340 itself should not depress significantly while the plunger 360 is being depressed, because the force required to move the low-viscosity fluid within the inner barrel should be less than the force required to move the high-viscosity fluid within the outer barrel through the needle. Rather, the force of the low-viscosity fluid in a circumferential manner about the sidewall of the outer barrel should eject some of the high-viscosity fluid through the needle until core annular flow is established.

In another method, the two fluids will naturally adopt a core annular arrangement if they undergo steady flow. When the low-viscosity fluid is injected into a flowing high-viscosity stream, the low-viscosity fluid naturally migrates to the wall to minimize stress (lower energy state) in a process called flow inversion. This results in core annular flow. Such arrangements can be accomplished by taking advantage of non-Newtonian fluid behaviors. For example, the low-viscosity fluid may be a lubricant that has a yield stress that is greater than what can be overcome by buoyancy forces (e.g. density difference between fluids).

Figure 4:
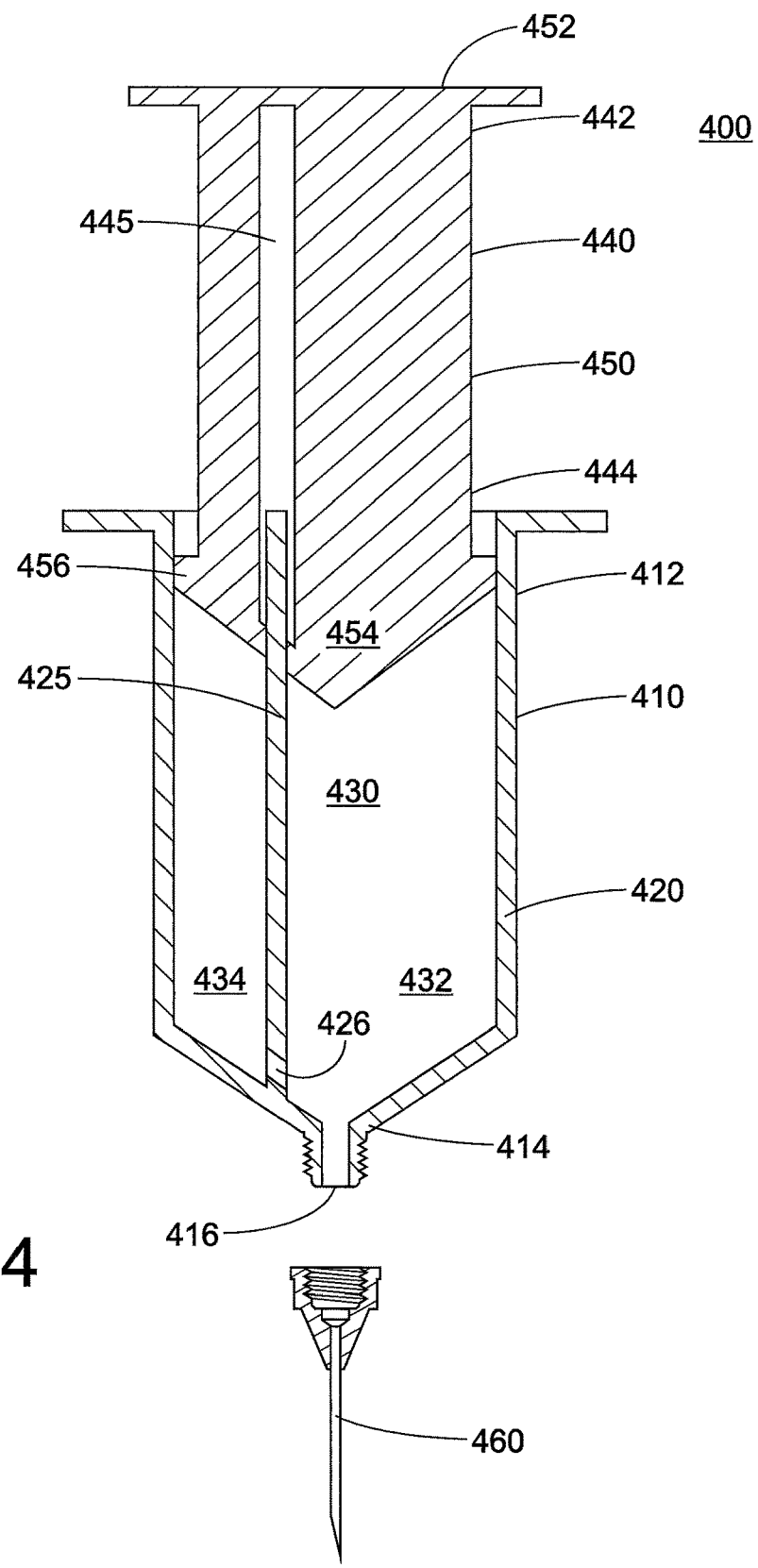
FIG. 4 is a diagram showing an injection device having two compartments, one for a high-viscosity fluid and one for a low-viscosity fluid. The compartments are formed from an inner wall running longitudinally within the barrel of the injection device.

FIG. 4 illustrates this method. Here, the injection device 400 is formed from a barrel 410, plunger 440, and needle 460. The barrel 410 is hollow and has a closed end 412 and an open end 414. The barrel is formed from a sidewall 420 that surrounds an interior space 430. The open end 414 includes an orifice 416 through which fluid exits the interior space 430, and to which the needle 460 is attached. An inner wall 425 is located inside the barrel that extends longitudinally between the open end 414 and the closed end 412. The inner wall 425 separates the interior space into a first compartment 432 and a second compartment 434. The inner wall is located to one side, so that the orifice 416 is wholly contained within the first compartment 432. There is a channel 426 located in the inner wall 425 that runs from the second compartment 434 into the first compartment 432, and the channel 426 is directed towards a circumference of the orifice 416. It is contemplated that the high-viscosity fluid will be located in the first compartment, and the low-viscosity fluid will be located in the second compartment. The second compartment may be relatively small, for example about 1% of the volume of the barrel. The plunger 440 includes a shaft 450 with a thumbrest 452 on one end 442 and two pistons 454, 456 on the other end 444. The plunger also contains a tunnel 445 that receives the inner wall 425 of the barrel. As seen here, a first piston 454 is located within the first compartment 432 and a second piston 456 is located within the second compartment 434.

In use, it is contemplated that pushing on the plunger 440 will cause both fluids to flow. The low-viscosity fluid is injected through the channel 426 of the inner wall into the high-viscosity fluid, and will naturally migrate against the wall of the needle to create core annular flow.

In a third method, it is possible to generate core annular flow using a phase change material as the low-viscosity fluid. For example, a thin coating of water is placed on the inside of the barrel or the needle, then captured in place by lowering the temperature to convert the water from its liquid phase into ice. In another section of the injection device, the high-viscosity fluid is captured. This filled injection device would be stored at a temperature below the phase change temperature (in this case, the melting point of the ice). Additives such as salts could be incorporated into the high-viscosity fluid to depress its melting point below that of the water. Upon use, applied heat from the user's hand or an external source would melt the ice, creating an annulus of low-viscosity fluid.

The core annular flow can be generated in either the injection device barrel, or the needle, or both.

It is known that suspensions (particles and fluid) will phase separate during flow. The particles will move to the center as the low-viscosity fluid moves to the walls. In the present disclosure, a distinct interface is created between the high-viscosity fluid and the low-viscosity fluid. The two fluids may be miscible, or even composed of the same solvent, but the interface will be present as a distinct boundary between the two fluids. Such a boundary may be defined, for example, by a step change in the concentration of solute in each fluid. The solute is defined as the species responsible for the viscosity, such as a high molecular weight protein. This distinct boundary is in contrast to the continuous concentration gradient that forms due to natural flow-induced phase separation in a suspension.

It is contemplated that the high-viscosity formulation can be a solution, dispersion, suspension, emulsion, etc. The high-viscosity formulation may contain a protein, such as a monoclonal antibody or some other protein which is therapeutically useful. The protein may have a concentration of from about 150 mg/mL to about 500 mg/mL. The high-viscosity formulation may have an absolute viscosity of from about 5 centipoise to about 1000 centipoise. The high-viscosity formulation may further contain a solvent or non-solvent, such as water, perfluoroalkane solvent, safflower oil, or benzyl benzoate.

The low-viscosity fluid may be water or an aqueous solution. Alternatively, the low-viscosity fluid may be an organic solvent appropriate for injection, such as a perfluoroalkane solvent, safflower oil, or benzyl benzoate. In embodiments, the low-viscosity fluid has a lower absolute viscosity than the high-viscosity formulation, and has an absolute viscosity of from about 0.3 to about 1000 centipoise.

The high-viscosity fluid and the low-viscosity fluid may be miscible or immiscible with each other.

It has been observed that the pressure reduction is proportional to the ratio of the viscosities of the two fluids. Put another way, an increased magnitude in the difference between the viscosities increases the pressure reduction. In some embodiments, the ratio of the viscosity of the high-viscosity formulation to the viscosity of the low-viscosity fluid (i.e. $\mu_H/\mu_L$) is from 1 to about 100 thousand, including from about 60 to about 200.

The velocities of the high-viscosity formulation and the low-viscosity fluid are substantially identical at the interface region, as required by physics. Desirably, the velocity gradient of the low-viscosity fluid (i.e. in the annular flow region) is greater than the velocity gradient of the high-viscosity formulation (i.e. in the core flow region). The velocity gradient may be determined theoretically by the equation of motion and rheological properties of the fluids. Velocity gradients can be determined experimentally by visual studies, such as particle image velocimetry of impulse injections of a dyed fluid, or by observation of a pressure drop.

Figures 5A, 5B:
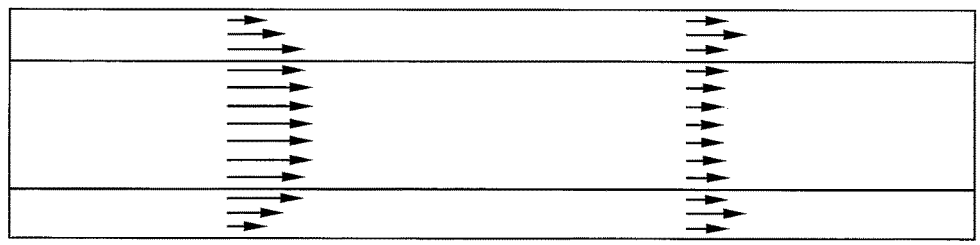
FIG. 5A is a first potential velocity profile for core annular flow, with a linear velocity profile in the annular fluid.
FIG. 5B is a second potential velocity profile for core annular flow, with a parabolic velocity profile in the annular fluid.

FIG. 5A and FIG. 5B show two potential velocity profiles for the core fluid (high-viscosity) and the annular fluid (low-viscosity). In FIG. 5A, the velocity of the annular fluid near the injection device barrel is lowest (no slip boundary condition at the wall), and the velocity increases linearly for the annular fluid as one moves away from the barrel wall towards the center of the barrel. At the core-annular fluid interface, the velocities are substantially identical. In FIG. 5B, the velocity profile of the annular fluid is parabolic, such as can occur in pressure driven flows. The velocity of the annular fluid is a maximum between the barrel wall and the interface region with a location that depends on the rheological behaviors of the fluids and the stresses placed on them.

The benefit of the processes of the present disclosure is supported with an analysis considering fully developed annular flow of Newtonian fluids in a cylindrical geometry. The governing equation relating the flow rate to the pressure drop is given by Equation (1):

$$Q = 2\pi \left[ \frac{-1}{16\mu_1} \frac{\Delta P}{L}(\lambda R)^4 + C\frac{(\lambda R)^2}{2} - \frac{1}{16\mu_2} \frac{\Delta P}{L}R^4 + \frac{1}{8\mu_2} \frac{\Delta P}{L}R^4 + \frac{1}{16\mu_2} \frac{\Delta P}{L}(\lambda R)^4 - \frac{1}{8\mu_2} \frac{\Delta P}{L}R^2(\lambda R)^2 \right]$$

$$C = \frac{1}{4\mu_1} \frac{\Delta P}{L}(\lambda R)^2 - \frac{1}{4\mu_2} \frac{\Delta P}{L}(\lambda R)^2 + \frac{1}{4\mu_2} \frac{\Delta P}{L}R^2$$

Equation (1)

where Q is the flow rate, $\Delta P/L$ is the pressure gradient, $\lambda$ is the fraction of the diameter occupied by the core fluid, R is the channel radius, and $\mu_1$ and $\mu_2$ are the viscosities of the core and the annular fluids, respectively.

Figure 6:
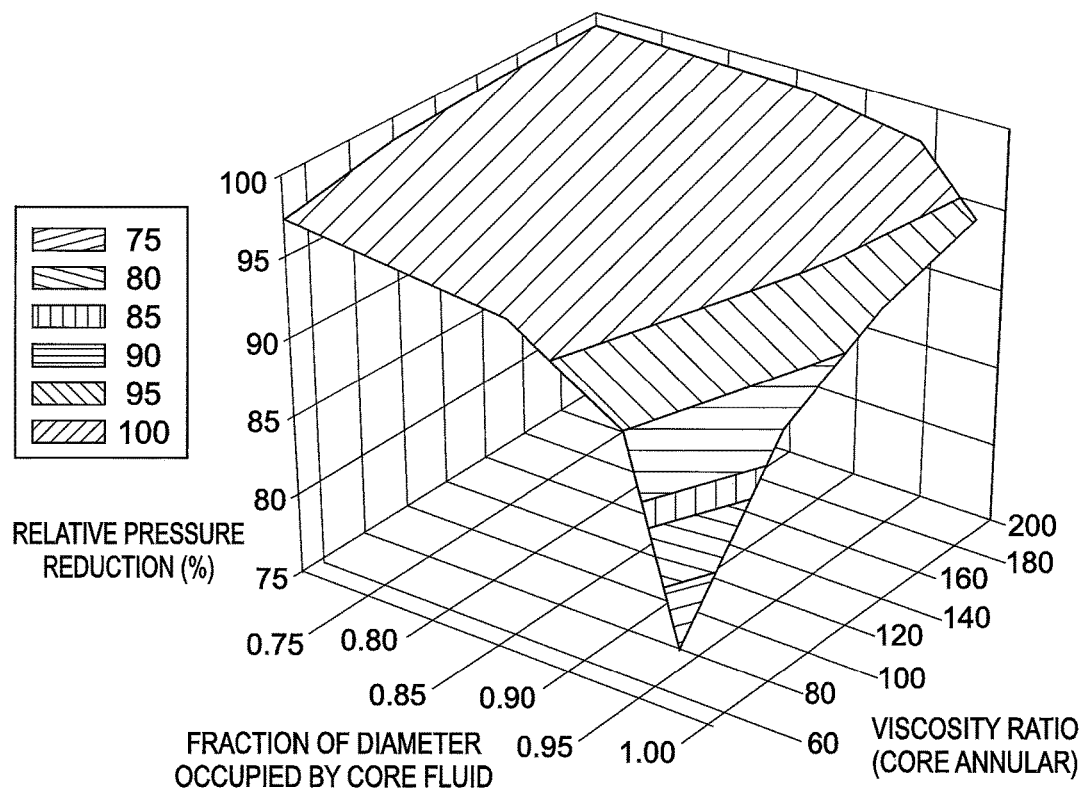
FIG. 6 is a graph showing the effect of the core fraction and the viscosity ratio on the pressure drop.
Figure 7:
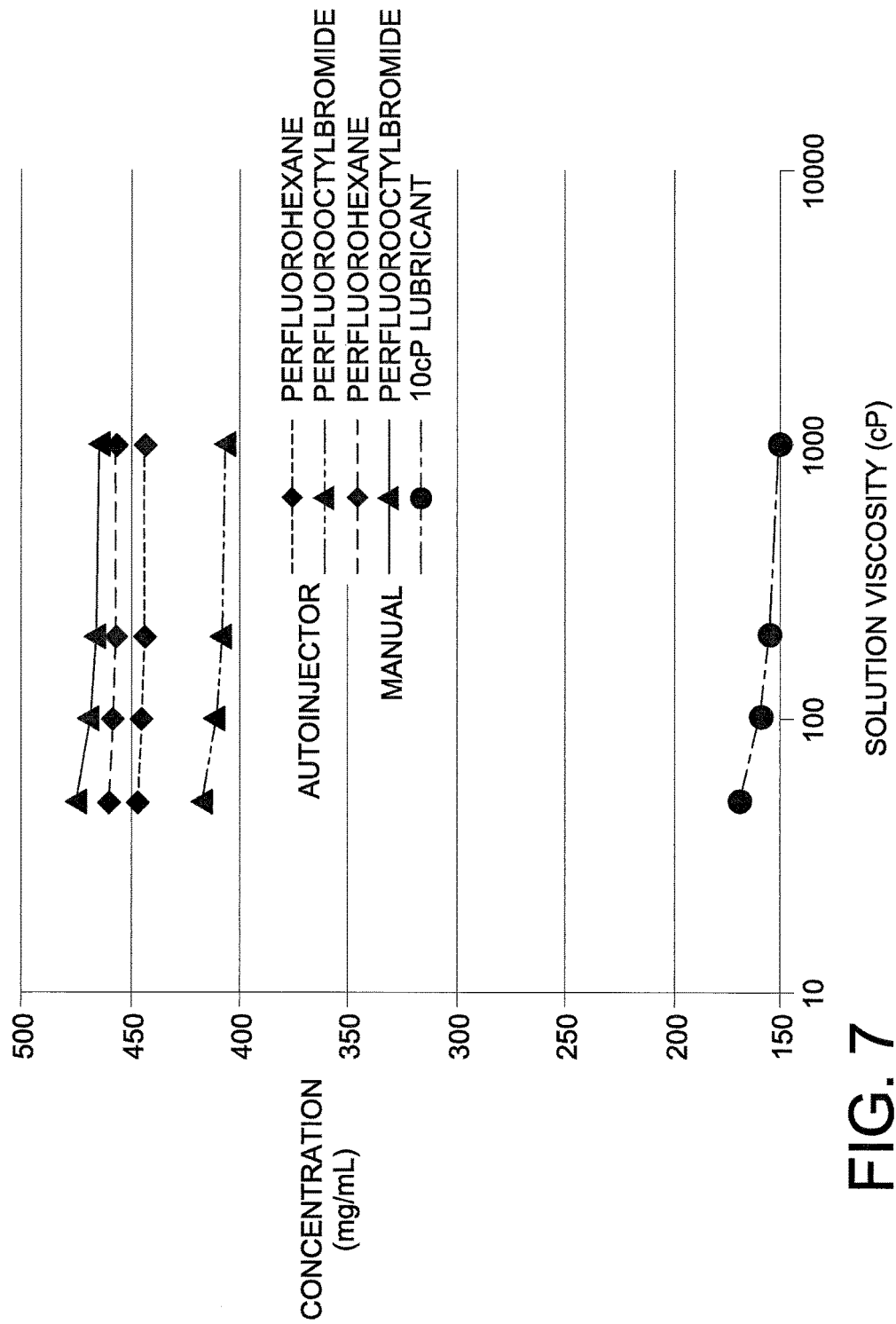
FIG. 7 is a graph showing the maximum concentration vs. viscosity obtainable when different low-viscosity fluids are used as an annular fluid for an auto-injector and a manual syringe.
Figure 8:
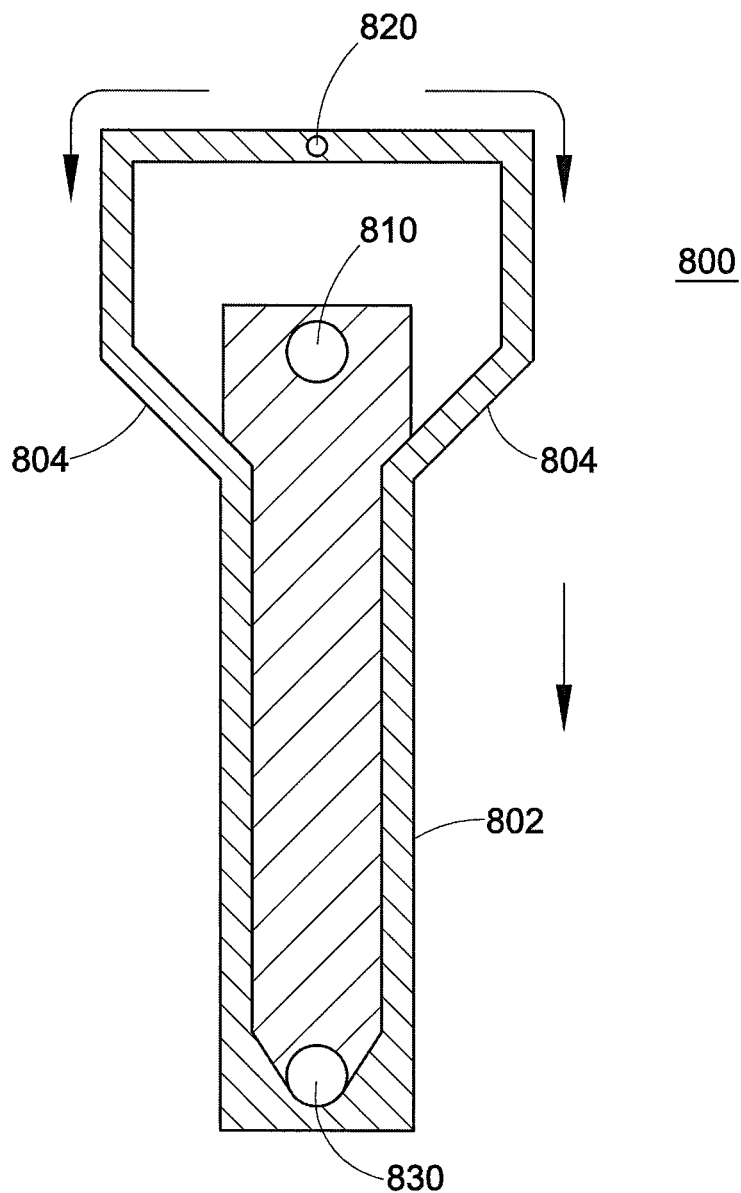

Results from the analysis are shown in FIG. 6. The benefit from core annular flow (pressure required to generate a given flow rate relative to the pressure required to produce the same flow rate without the annular fluid) is shown for a series of Newtonian fluids (viscosity ratios) and annular layer thicknesses. These results are subject to the constraints of the Newtonian assumption and are expressed in relative terms, so the benefit is independent of flow rate and channel width. The results indicate that the pressure reduction is greatest for large viscosity ratios and large lubricant thicknesses. It should be noted that the dependence on those variables, especially $\lambda$, is nonlinear, indicating that significant benefit can be realized even for thin annular layers and lower viscosity core fluids. The highest pressure reduction obtained was 99.3% at a core fraction of 70% and a viscosity ratio of 200. At a viscosity ratio of 1 or a core fraction of 1, the relative pressure reduction was zero.

As seen in FIG. 6, the core fraction, i.e. the cross-sectional area occupied by the core fluid, affects the pressure drop. In embodiments, the fraction of the width of the injection device barrel occupied by the high-viscosity formulation is from about 0.70 to less than 1. The fraction is always less than 1. It should be noted that in a cylindrical barrel, the width of the injection device barrel is the diameter of the cylinder.

The required injection force to inject a protein formulation of a given concentration or viscosity is reduced by the processes of the present disclosure. In embodiments, the high-viscosity pharmaceutical formulation is injected with a force of 20 newtons or less. In embodiments, the high-viscosity pharmaceutical formulation is injected within an injection time of 30 seconds or less.

The embodiment depicted in FIG. 2 may be considered to have a finite volume of the low-viscosity fluid. In another preferred embodiment, the low-viscosity fluid in the annular region is replenished from an external source while the plunger is being depressed, or in other words during the injection of the high-viscosity fluid or during the dispensing process. This would allow for additional flow control to deliver a relatively constant ratio of core fluid to lubricant (within the context of an Eulerian reference frame) to be maintained.

Figure 10:
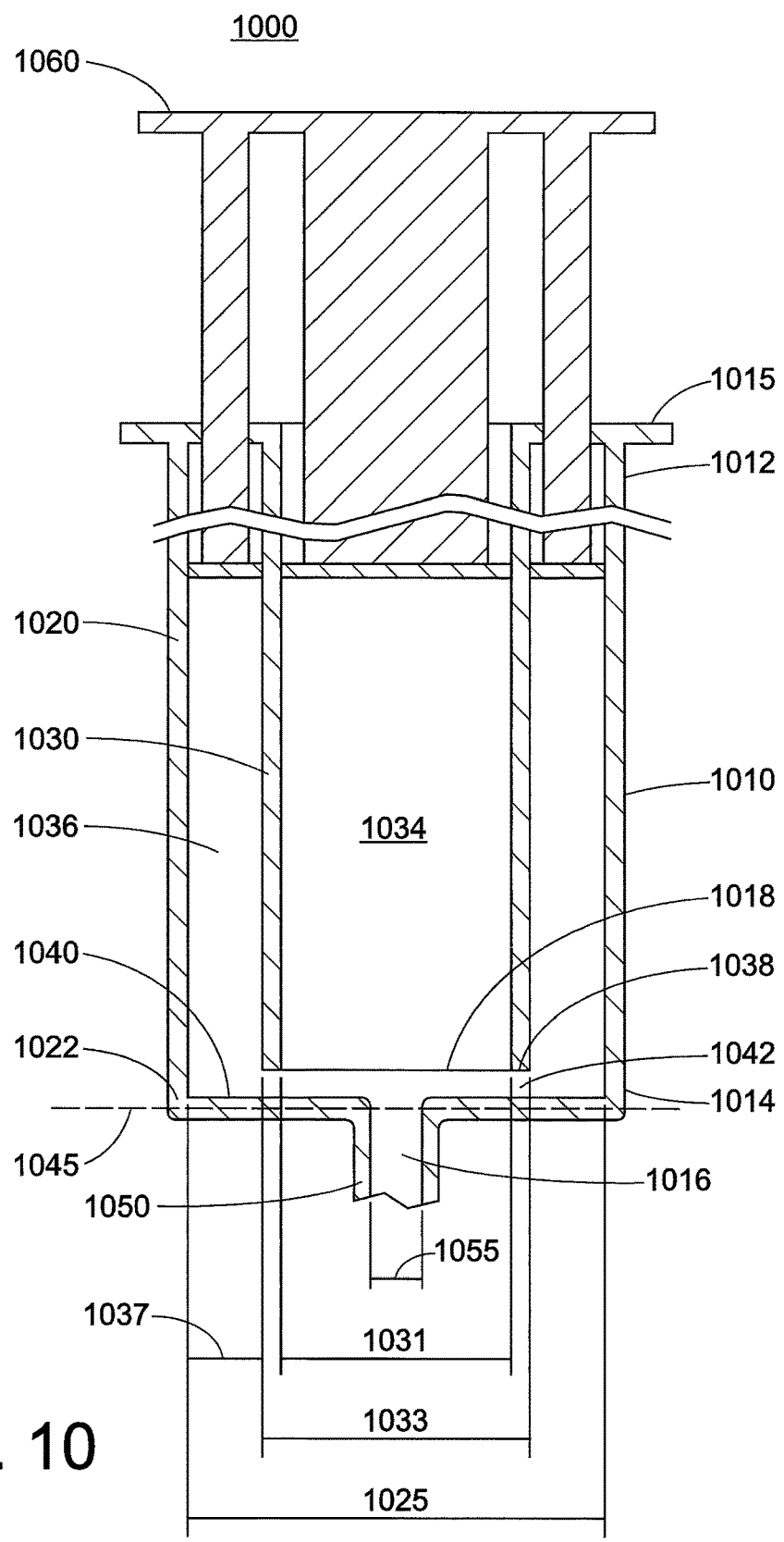

Another embodiment of an injection device 1000 which is capable of core annular flow is depicted in FIG. 10. The needle is not depicted here. The barrel 1010 is hollow, and has an open end/needle end 1014 and a closed end/plunger end 1012. A finger flange 1015 is located at the closed end of the barrel.

The barrel 1010 is formed from a sidewall 1020 that has an internal diameter 1025. An inner concentric wall 1030 is located within the barrel. An inner compartment 1034 and an outer compartment 1036 within the barrel are defined by the inner concentric wall. In this regard, the inner compartment 1034 has an inner diameter 1031 equal to the internal diameter of the concentric wall. The outer compartment has an annular shape, with a width 1037 that is the difference between the internal diameter 1031 of the sidewall and the external diameter 1033 of the inner concentric wall.

The open end 1014 of the barrel includes a front wall 1040 that extends from a constriction point 1022 to an orifice 1016. The "constriction point" is used here to refer to the location on the sidewall 1020 where the barrel begins to reduce from the internal diameter 1025 down to a smaller diameter for fluid to be injected through the orifice 1016. As illustrated here, the constriction point 1022 is the intersection of the sidewall 1020 and the front wall 1040, with the front wall being located in essentially a radial plane (reference numeral 1045). A nipple 1050 is present at the open end 1014 of the barrel to which the needle is attached. The nipple has a smaller diameter 1055 than the barrel 1025.

The inner concentric wall 1030 includes a bottom edge 1038. An opening 1042 is formed between the inner concentric wall 1030 and the front wall 1040, which permits fluid in the outer compartment 1036 to flow towards the orifice 1016 when the plunger is depressed. Here in FIG. 10, the opening is a vertical opening. The inner concentric wall 1030 is not connected to the front wall 1040, but rather is supported at the closed end 1012 of the barrel.

Figure 11:
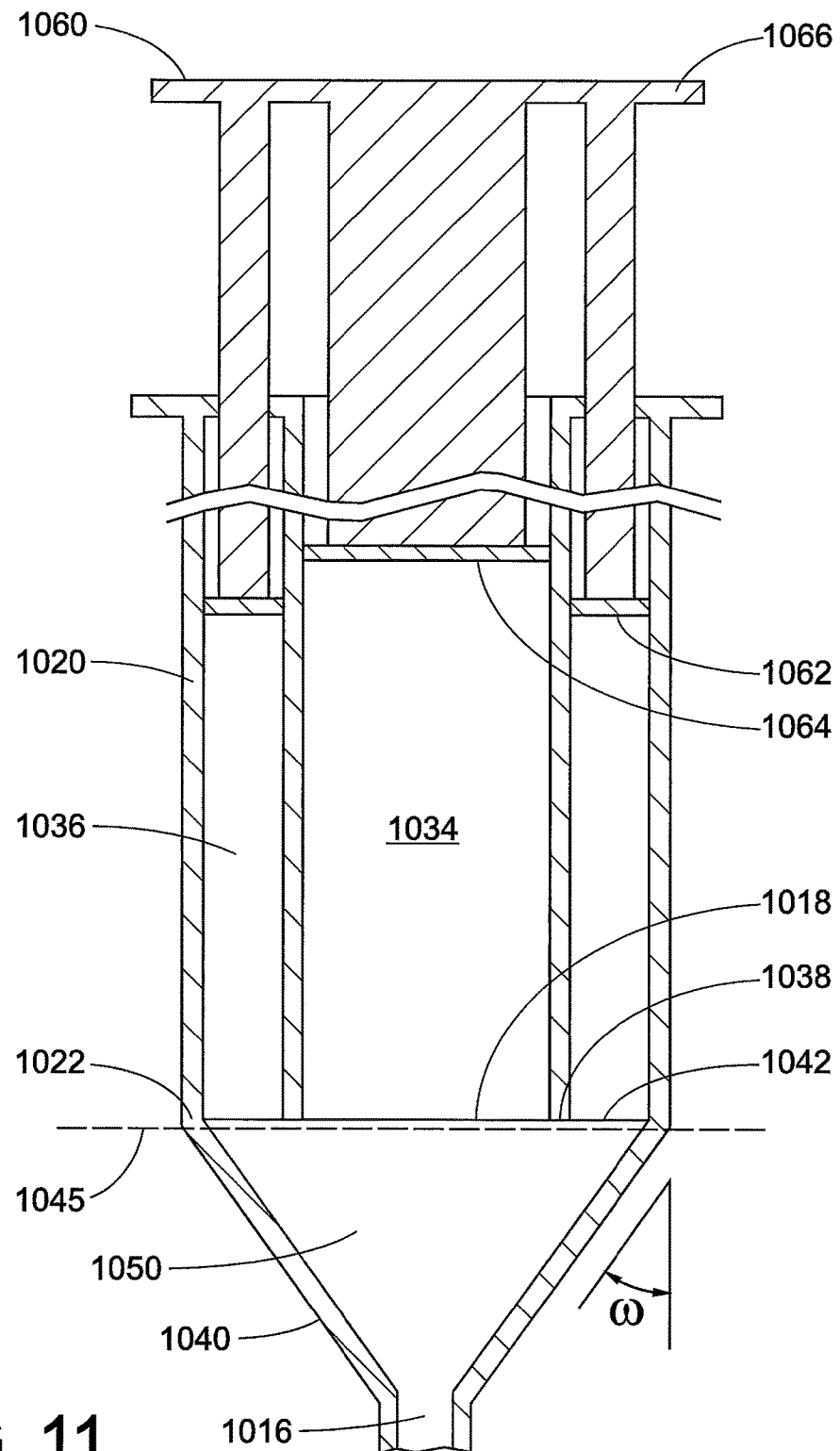

FIG. 11 is a variation on FIG. 10. Here, the front wall 1040 in FIG. 11 can be described as tapering from the constriction point 1022 to the orifice 1016, from a larger diameter to a smaller diameter. The bottom edge 1038 of the inner concentric wall and the constriction point are located about the same radial plane 1045. Here, the opening 1042 that permits fluid in the outer compartment to flow is a radial opening. The degree of tapering is measured longitudinally, and is denoted here as angle $\omega$. In particular embodiments, the angle $\omega$ is from about 20° to about 45°, and in some specific embodiments is about 30°.

In the embodiments of FIG. 10 and FIG. 11, the plunger 1060 provides a depressing force concurrently to the inner compartment 1034 and the outer compartment 1036. The low-viscosity fluid flows preferentially against the wall of the barrel, so that the high-viscosity fluid is in the core and does not contact the wall.

Desirably, the volume ratio of high-viscosity fluid to low-viscosity fluid is as high as possible, since it is the high-viscosity fluid that delivers the desired medication and the low-viscosity fluid essentially serves as a lubricant within the injection device. The radial cross-sectional areas of the inner compartment 1034 and the outer compartment 1036 can be controlled to control the volumetric flow of the two fluids. In this regard, the cross-sectional areas for the two compartments can be determined using the interior diameter of the concentric wall, the internal diameter of the sidewall, and the exterior diameter of the inner concentric wall. In embodiments, the ratio of the cross-sectional area of the inner compartment to the cross-sectional area of the outer compartment is from about 2:1 to about 9:1. In ideal circumstances, the flows of the low-viscosity and high-viscosity fluids meet at the constriction point.

A means for sealing, such as a sealing membrane, may be used to locate the low-viscosity fluid and the high-viscosity fluid in desired locations prior to the injection device being used (or the plunger being depressed), or to keep the two fluids separated to prevent mixing during storage. In FIG. 10, a sealing membrane 1018 is located across only the inner concentric wall 1030, to separate the inner compartment 1034 from the outer compartment 1036 and the nipple 1050. It is contemplated that the nipple is filled with only the low-viscosity fluid.

In FIG. 11, the sealing means 1018 is located across the barrel sidewall 1020 at approximately the constriction point 1022, so that the inner compartment 1034 and the outer compartment 1036 are separated from the nipple 1050. Again, the nipple is filled with only the low-viscosity fluid.

Figure 12:
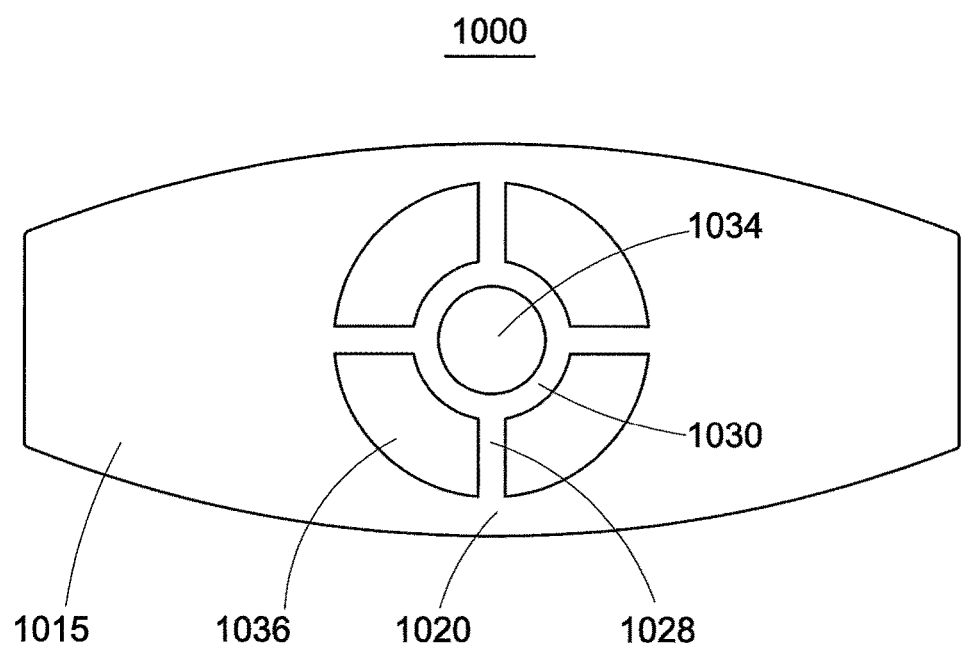

FIG. 12 is a top view of the closed end of the barrel, with the plunger removed so the structure can be seen. As seen here, the inner concentric wall 1030 is connected to the barrel sidewall 1020 and supported by radial walls 1028. Finger flange 1015 extends from the sidewall 1020.

Two different types of plungers are contemplated. In FIG. 10, the plunger 1060 is constructed so that the high-viscosity fluid and low-viscosity fluid are pushed together at the same time and at the same rate. In FIG. 11, the plunger 1060 is designed to push some low-viscosity fluid out before the high-viscosity fluid is pushed out. As seen here, the piston 1062 in the outer compartment is at a lower level compared to the piston 1064 in the inner compartment. Put another way, the piston 1062 of the outer compartment is located further from the thumbrest 1066 than the piston 1064 in the inner compartment. In this embodiment, there is usually air between the piston 1064 and the fluid. Thus, some of the high-viscosity fluid generally remains within the injection device after the plunger is fully depressed so that air is not injected.

Figure 13:
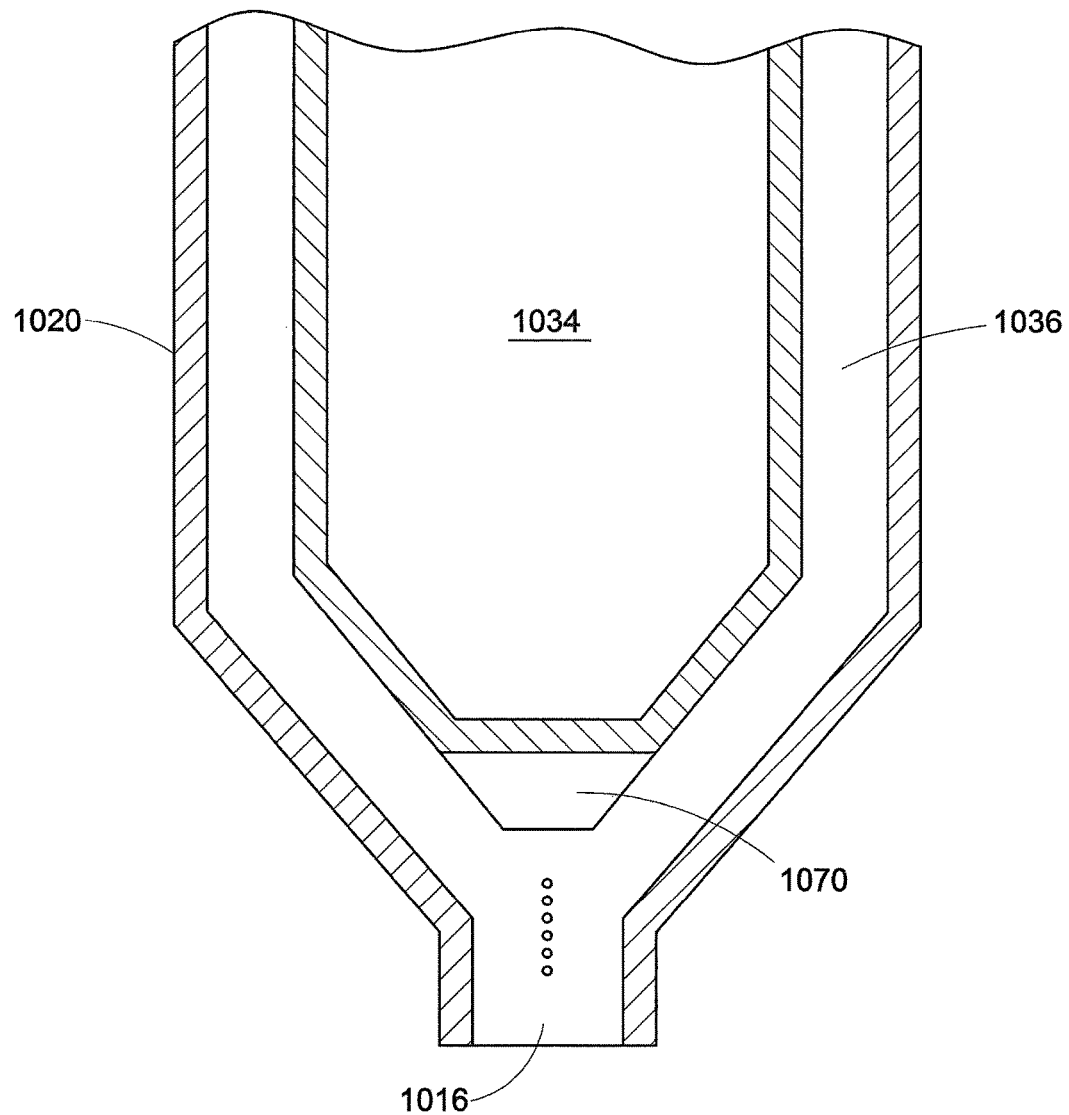

Another variation is shown in FIG. 13. In this variation, the inner compartment 1034 is closed at the bottom by a valve mechanism 1070. Again, the high-viscosity fluid is located within the inner compartment 1034 and the low-viscosity fluid is contained in the outer compartment 1036. When the plunger is depressed, the valve mechanism operates to release the high-viscosity fluid as a series of small drops which can be surrounded by the low-viscosity fluid, so that core annular flow occurs.

Figure 14:
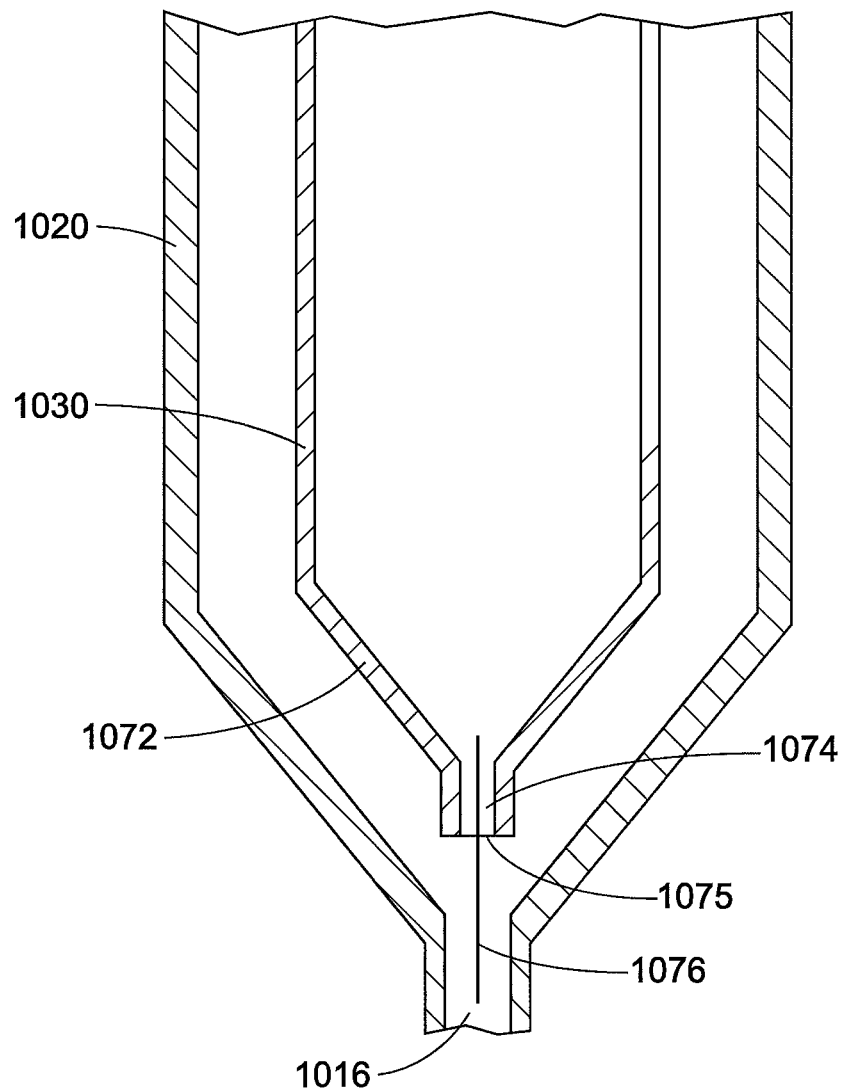

In another variation, illustrated in FIG. 14, the inner concentric wall 1030 includes a lower wall 1072 that is tapered to form an aperture 1074. A means for sealing 1075, such as a sealing membrane or a valve, is located at the aperture. This embodiment can be described as a "syringe within a syringe". When the plunger is depressed, the sealing means is ruptured and injection of the high-viscosity fluid begins. In some embodiments, a wire 1076 may be present along the longitudinal axis. It is contemplated that the high-viscosity fluid will preferentially "attach" to the wire, which aids in maintaining the core annular flow of the injection device. The wire can be supported by the wall 1030, 1072.

Figure 15:
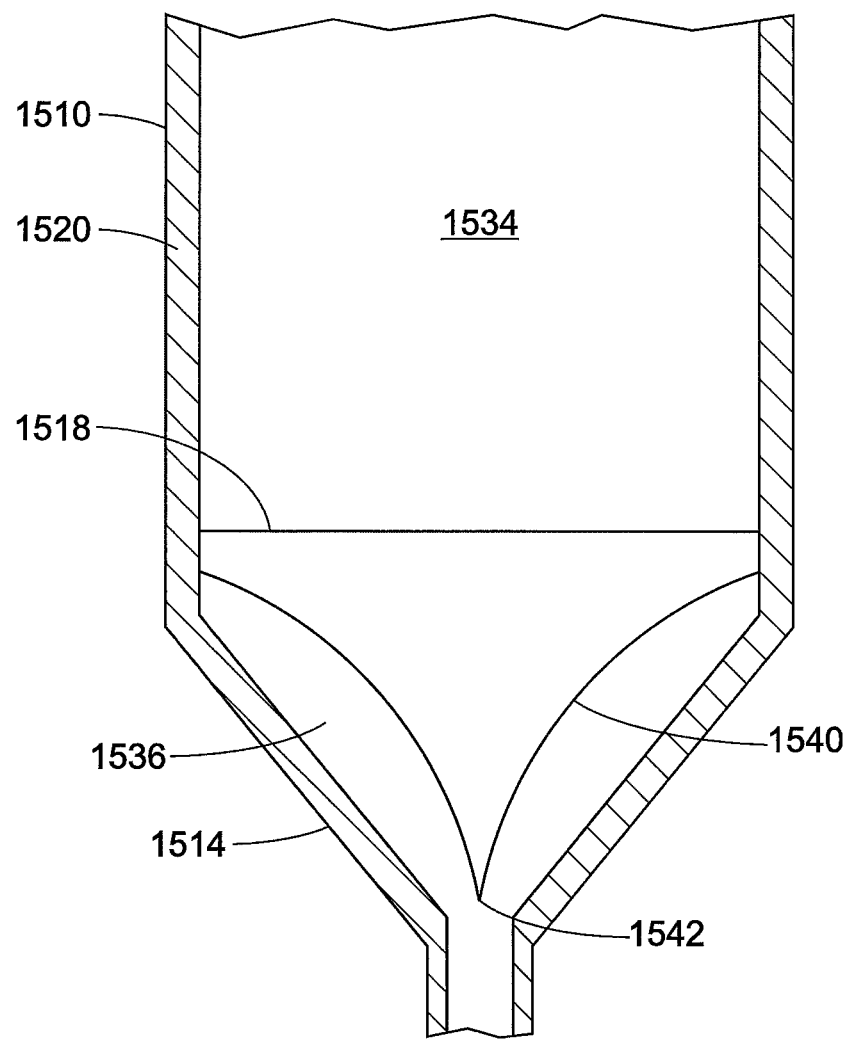

Another embodiment of an injection device that is capable of core annular flow is illustrated in FIG. 15. This figure focuses on the open end 1514 of the barrel 1510, and the plunger and the needle are not shown. A sealing membrane or film barrier 1518 is located here, which separates the internal volume of the barrel into an upper compartment 1534 and a lower compartment 1536. The high-viscosity fluid is located in the upper compartment 1534. A wetted foil pouch 1540 is present in the lower compartment, which is connected at its upper end to the sidewall 1520. The foil pouch is configured so that it can expand upon the application of pressure, i.e. is an expandable pouch. The bottom 1542 of the expandable pouch 1540 is configured to preferentially split open upon the application of pressure beyond a given threshold value. The expandable pouch contains low-viscosity fluid. When pressure is applied (by pressing the plunger), the sealing membrane/film barrier 1518 ruptures and the high-viscosity fluid enters the expandable pouch 1540. The bottom of the expandable pouch 1542 then ruptures. The low-viscosity fluid is adjacent the sides of the pouch, and lubricates the flow of the high-viscosity fluid, creating core annular flow.

Figure 16:
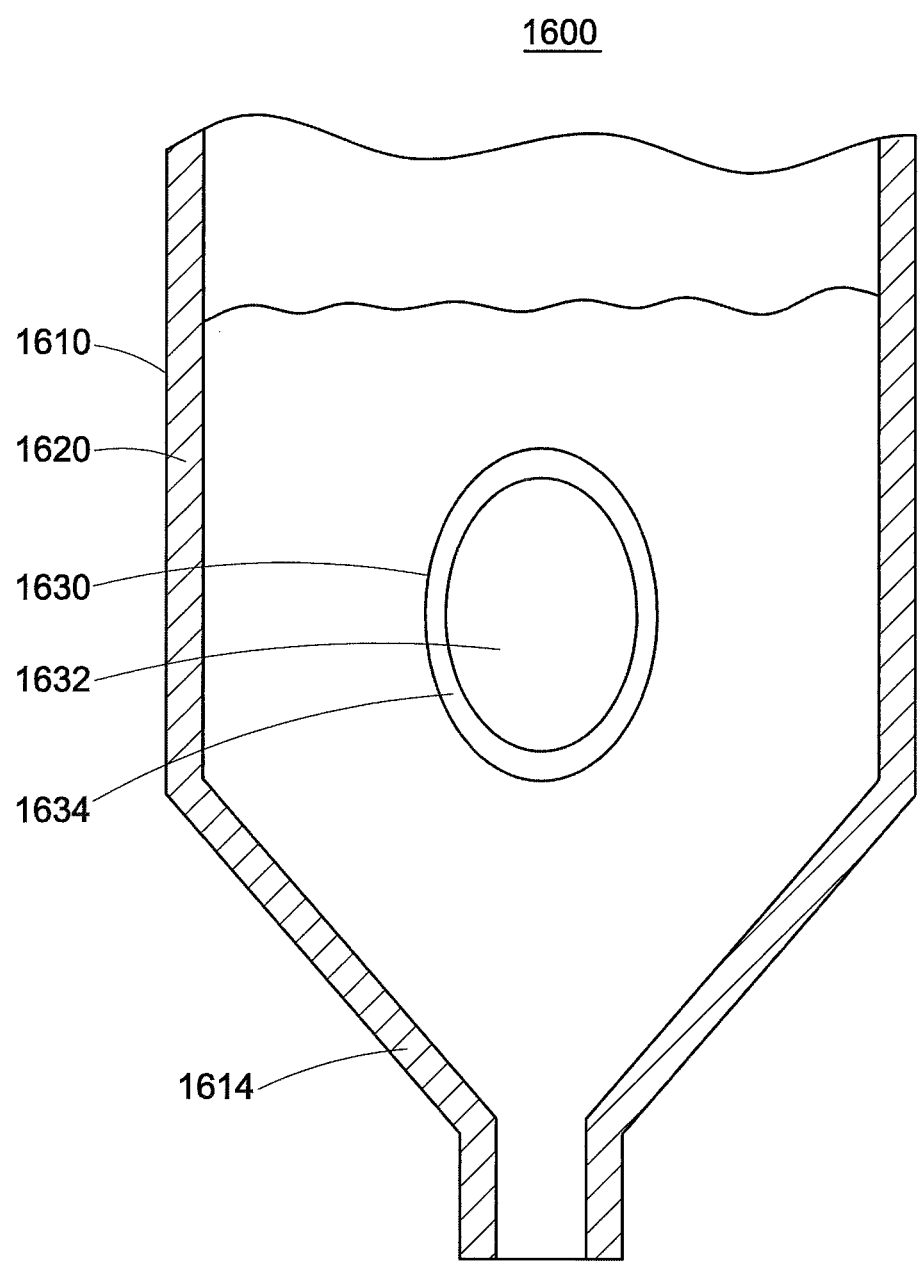

FIG. 16 illustrates another embodiment in which an injection device 1600 can be made capable of core annular flow. The barrel 1610 is formed from a sidewall 1620 and has an open end 1614. The concept here is that the high-viscosity fluid is provided as a bead 1630, having a core 1632 with a shell 1634 surrounding the high-viscosity fluid. The shell is used to separate the high-viscosity fluid (in core 1632) from the low-viscosity fluid until the injection device is used. The shell is then broken and core annular flow can occur.

In this regard, it is contemplated that the injection device here can be a conventional syringe, as seen in FIG. 1. The bead 1630 containing the high-viscosity fluid core is deposited into the barrel 1610 of the injection device by removing the plunger. The plunger is then depressed towards the open end 1614, and can be filled with low-viscosity fluid through the open end. Any air in the barrel can be removed by flipping the injection device needle-side up and pushing the plunger in.

Different shells are contemplated for the bead containing the high-viscosity fluid. In some embodiments, the shell is a biocompatible polymer that is insoluble in the low-viscosity fluid. This shell could be cracked or broken by the application of an external force. For example, acoustic cavitation or a laser could be used to penetrate the shell once the bead is within the low-viscosity fluid. Alternatively, the shell could be made from a material that is soluble in the low-viscosity fluid. In such embodiments, it is contemplated that upon dissolution of the shell, the low-viscosity fluid and high-viscosity fluid would be immediately injected into the patient (so that the two fluids do not mix together).

Figure 17:
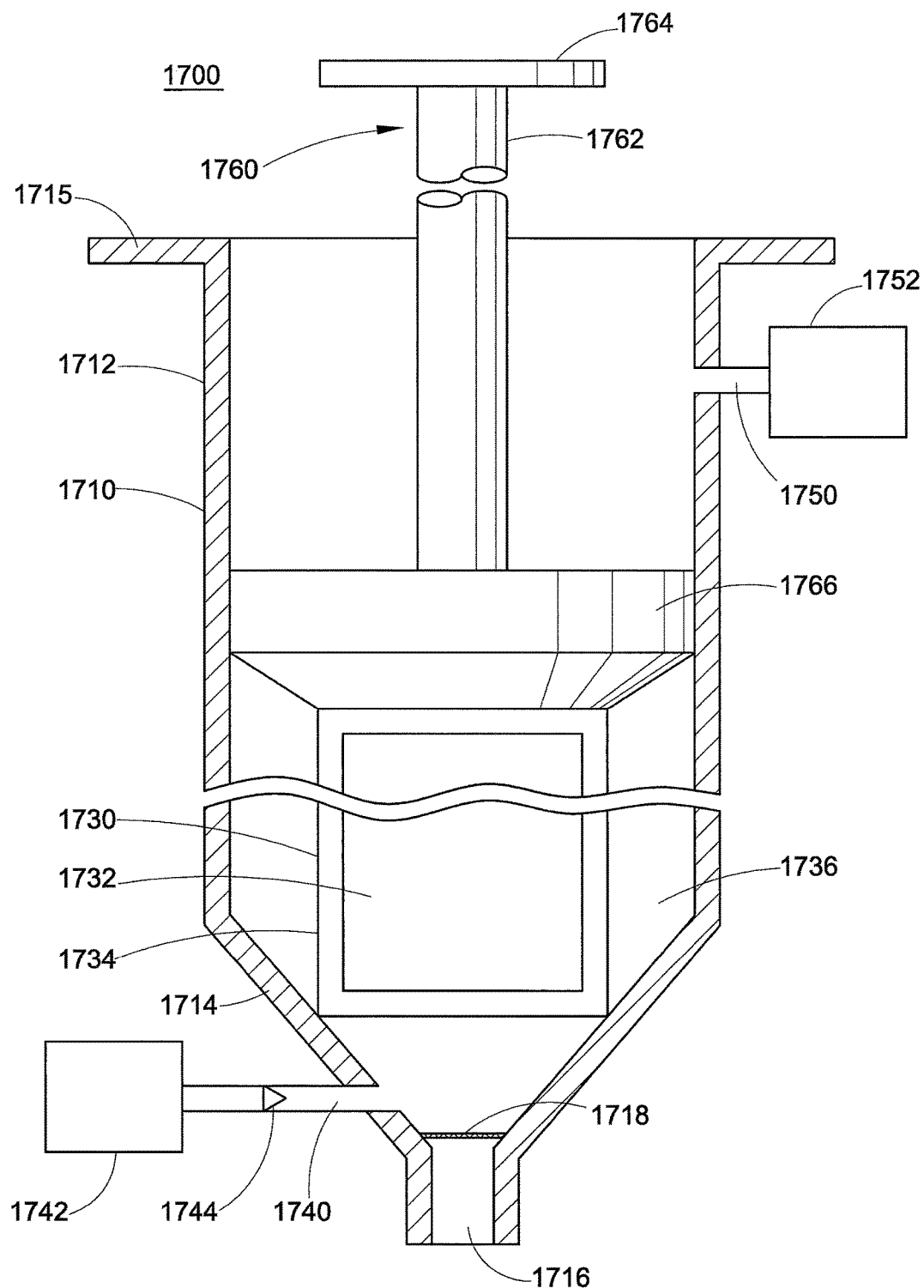

FIG. 17 shows another injection device 1700 that can be used for core annular flow. The barrel 1710 is hollow, and has an open end/needle end 1714 and a closed end/plunger end 1712. A finger flange 1715 is located at the closed end of the barrel. In this embodiment, the barrel 1710 of the injection device contains the high-viscosity fluid. The high-viscosity fluid is in the form of a bead 1730, having a core 1732 with a shell 1734 surrounding the high-viscosity fluid as described above. The bead is constructed such that an open annulus 1736 is present within the barrel around the bead (e.g. the bead may be in the shape of an X). The cross-sectional area of the annulus should be larger than the orifice 1716 that leads to the needle. Alternatively, the orifice 1716 to the needle can be closed off with a means for sealing 1718, such as a sealing membrane or valve.

While the barrel already includes openings for the needle (1716) and for the plunger (1712), one additional opening is also present. An inlet 1740 is present at the open end of the injection device and is connected to a fluid reservoir 1742 containing the low-viscosity fluid. In this embodiment, the low-viscosity fluid is stored in the fluid reservoir and the high-viscosity fluid is stored in the form of a bead in the barrel until the injection device is to be used. The injection device 1700 is also stored with the plunger 1760 being partially depressed within the barrel. As illustrated here, the plunger 1760 is a shaft 1762 with a thumbrest 1764 on one end and a piston 1766 at the other end (shown here as resting upon the bead 1730). To prevent flow of the low-viscosity fluid into the barrel, the inlet 1740 may be closed off with a means for closing 1744, such as a sealing membrane (not depicted) or a one-way valve that only permits flow in the direction from the fluid reservoir into the barrel.

It is contemplated that the injection device is used by first pulling the plunger 1760 out of the barrel 1710. This creates low pressure within the barrel, causing the closing means 1744 to open, i.e. the sealing membrane would be broken or the one-way valve would open. This permits the low-viscosity fluid to enter the barrel and fill the annulus 1736 surrounding the bead of high-viscosity fluid. The low-viscosity fluid rises and surrounds the bead 1730 containing the high-viscosity fluid. The shell 1734 dissolves upon exposure to the low-viscosity fluid, releasing the core of high-viscosity fluid. The plunger 1760 is then depressed (pushed into the barrel), and core annular flow occurs. If the orifice 1716 is sealed off, the pressure will break the seal and permit the fluids to flow into the needle. It is contemplated that the plunger may be shaped so that it cannot entirely depress, leaving some fluid within the injection device. This ensures that any air in the injection device is not injected into the user.

If desired, an outlet 1750 can be located at the closed end of the injection device, which is connected to an outlet reservoir 1752. It is contemplated that the injection device could be used with beads of different sizes, in which case the needed amount of low-viscosity fluid may vary. If the amount of low-viscosity fluid is too great for the bead that is used, the extra fluid could flow into the outlet reservoir. When present, the fluid reservoir and outlet reservoir can be placed in any orientation around the barrel relative to each other, for example on the same side or on opposite sides. There should be sufficient room left between the finger flange 1715 and the outlet reservoir 1750 to accept the finger of the user.

Figure 18:
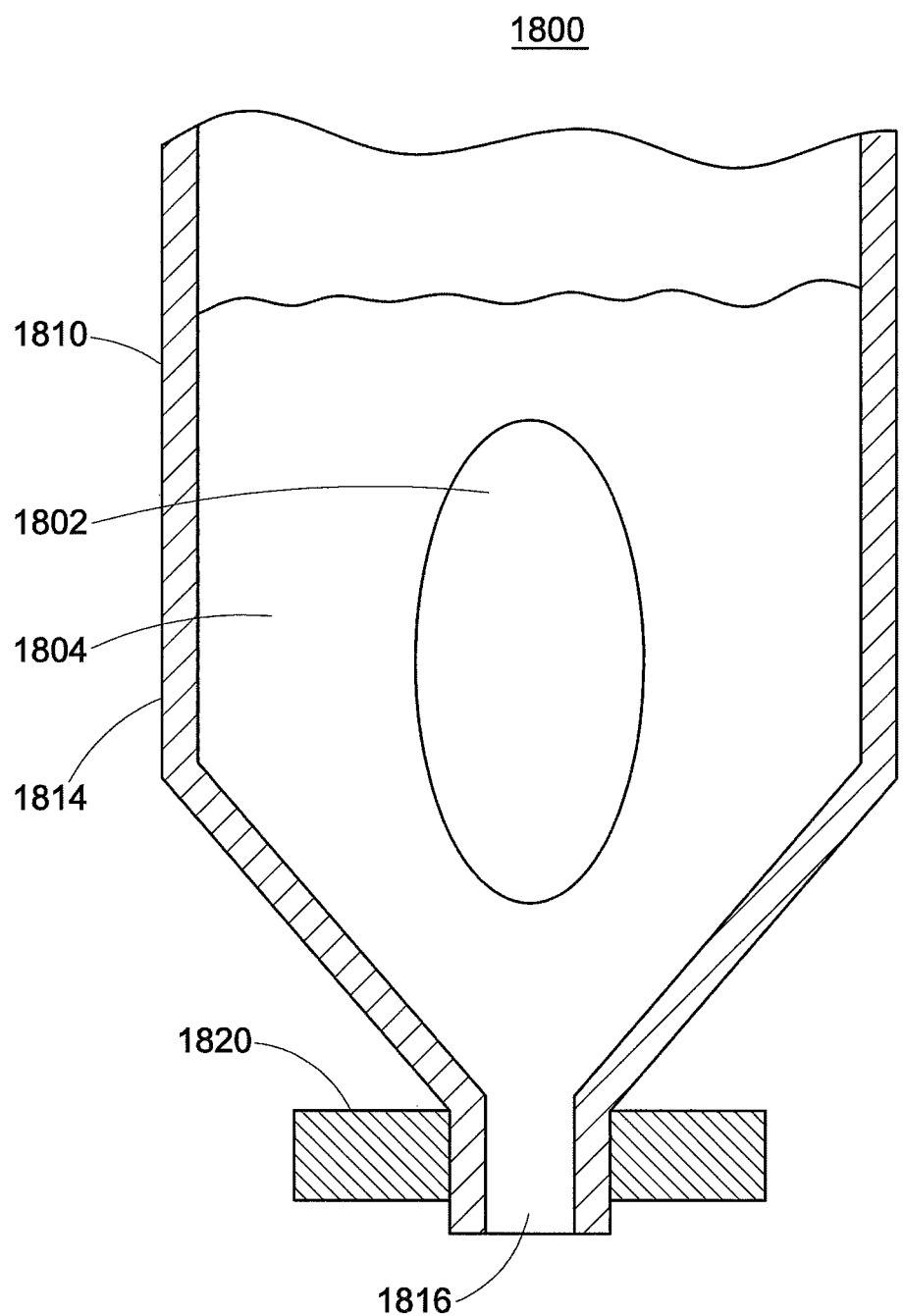

FIG. 18 describes another injection device 1800 that can be used for core annular flow. In this view, the open end 1814 of the injection device is magnified. Low-viscosity fluid 1804 and high-viscosity fluid 1802 are present in the barrel 1810, with the low-viscosity fluid surrounding the high-viscosity fluid. At the open end of the barrel is a sonic generator 1820 that surrounds the orifice 1816 through which fluid flows into the needle. The sonic generator creates sound waves that travel radially inwards through the material making up the barrel towards the longitudinal axis of the injection device. It is contemplated that the sound waves can create a "wall" of pressure that prevents high-viscosity fluid from contacting the sides of the orifice. This minimizes flow resistance, permitting core annular flow. Alternatively, the vibrations created by the sound waves may reduce the viscosity of the high-viscosity fluid, minimizing flow resistance and permitting it to flow more easily. The high-viscosity fluid can be stored in the form of a core/shell bead as previously described, or can be added in any of the other variations described herein.

Figure 19:
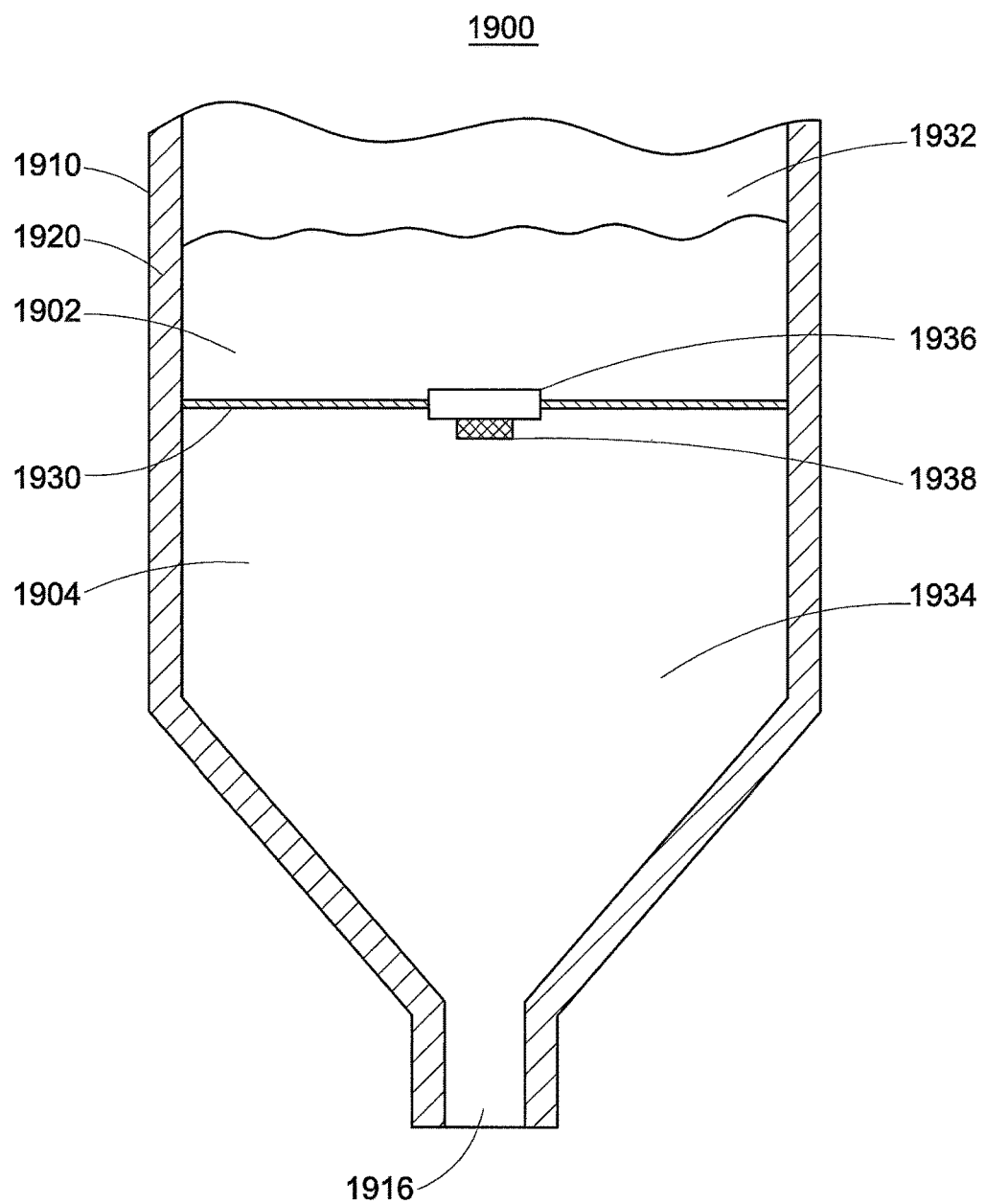
Figure 20:
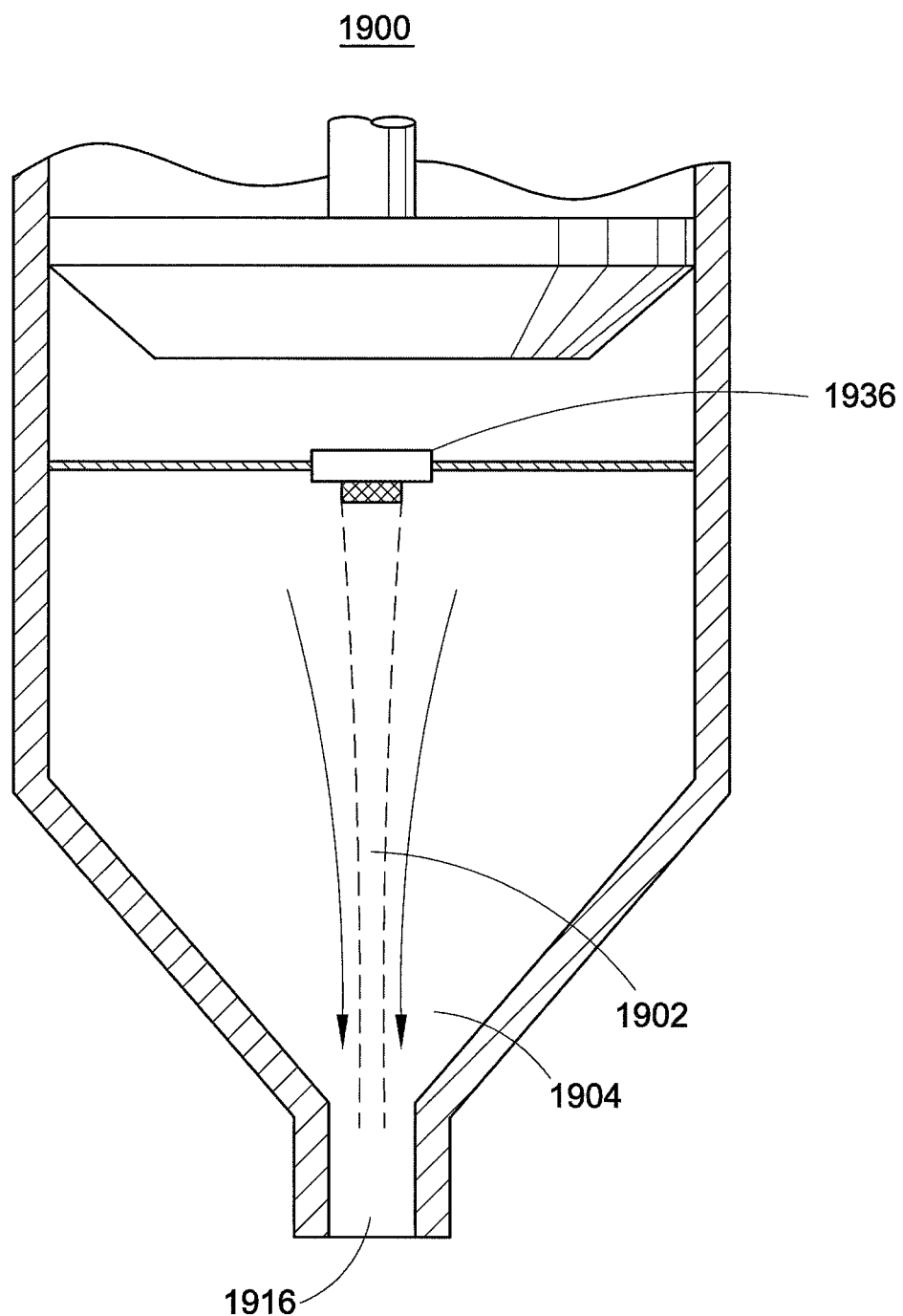

FIG. 19 and FIG. 20 show another variation of an injection device 1900 that provides for core annular flow. The barrel 1910 is formed from a sidewall 1920. Here, a floor 1930 is present in the barrel. In contrast to for example the membrane in FIG. 15, the floor here is relatively solid or rigid, and is not intended to break. The floor extends radially to the sidewall 1920, separating the barrel into an upper compartment 1932 and a lower compartment 1934. An aperture 1936 is present in the center of the floor, and is aligned with the orifice 1916 leading to the needle. The aperture is sealed with a sealing means 1938, for example with a sealing membrane or a valve. The high-viscosity fluid 1902 is present in the upper compartment 1932, and the low-viscosity fluid 1904 is present in the lower compartment 1934.

As illustrated in FIG. 20, when the plunger is depressed, the high-viscosity fluid 1902 is pushed through the aperture 1936 and shoots through the low-viscosity fluid 1904 into the needle. The low-viscosity fluid is "pulled" along with the high-viscosity fluid (represented by the arrows) so that core annular flow occurs.

Figure 21:
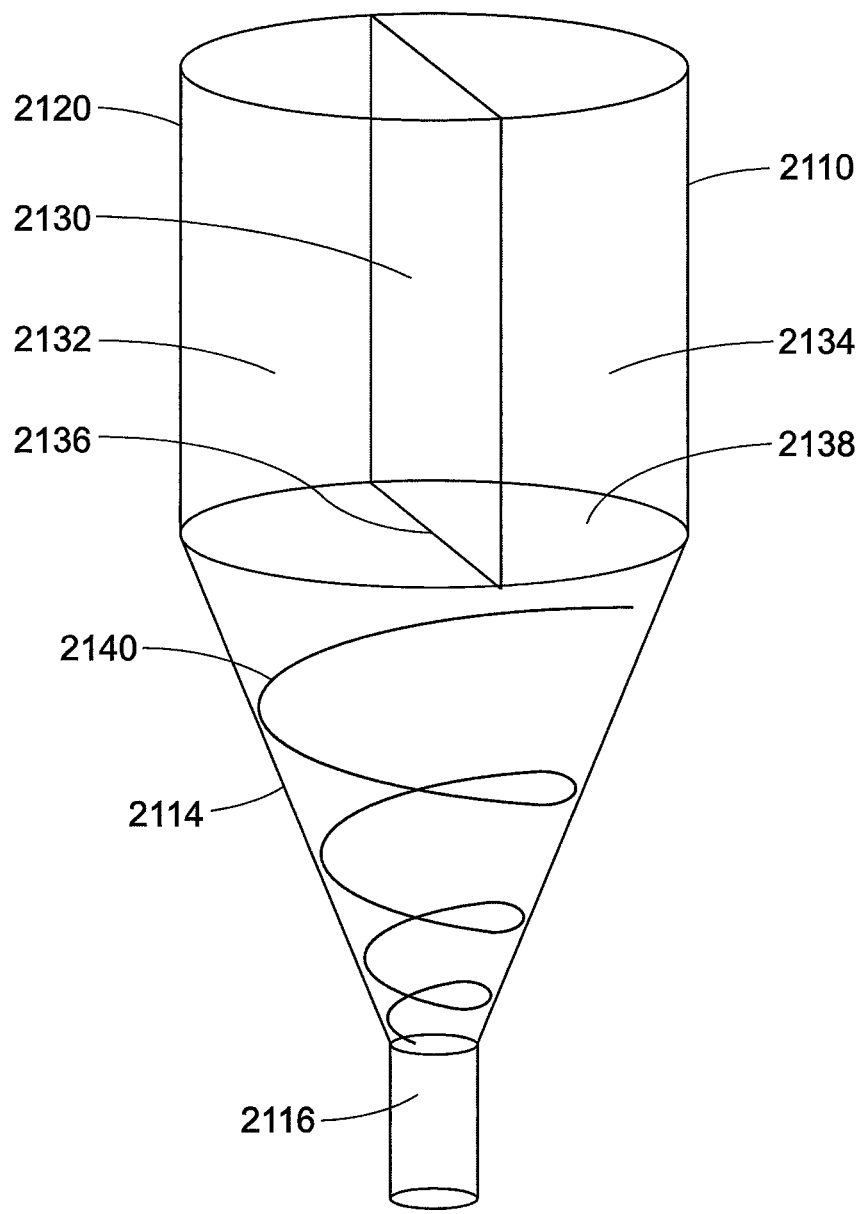

FIG. 21 illustrates an additional concept that can be applied to many of the embodiments described above. In many embodiments, the low-viscosity fluid is separated from the high-viscosity fluid, and the two fluids are brought together during injection. In this figure, the barrel 2110 is formed from a sidewall 2120. An inner wall 2130 is present that divides the barrel into a first compartment 2132 and a second compartment 2134. The bottom edge 2136 of the inner wall is free hanging, i.e. does not attach to another wall. A sealing means 2138 (e.g. a membrane) is present at the bottom edge 2136 of the inner wall. Grooves 2140 may be etched into the sidewall area of the open end 2114 of the injection device leading to the orifice 2116. It is contemplated that such grooves will encourage the low-viscosity fluid to migrate to the boundary, encouraging the development of core annular flow.

Figure 22:
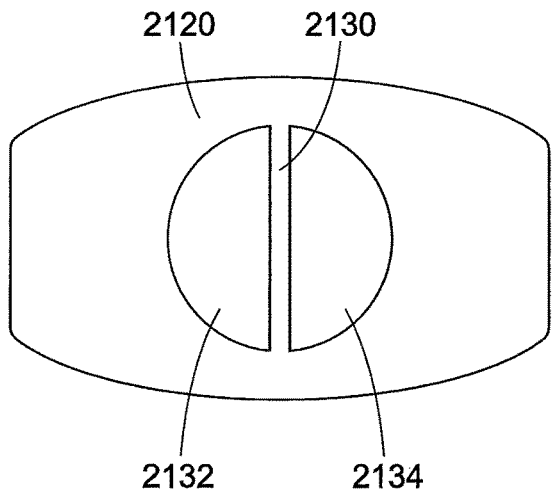
Figure 23:
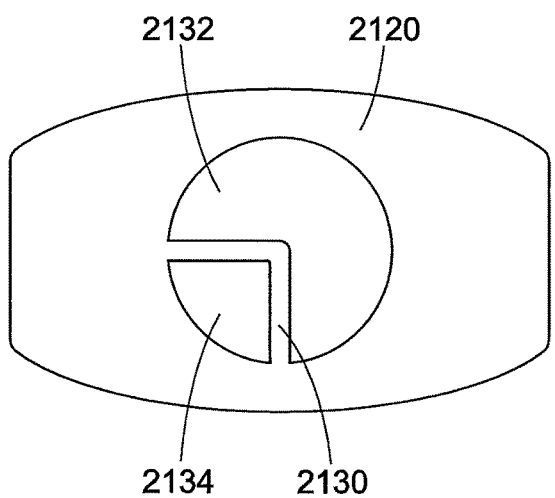
Figure 24:
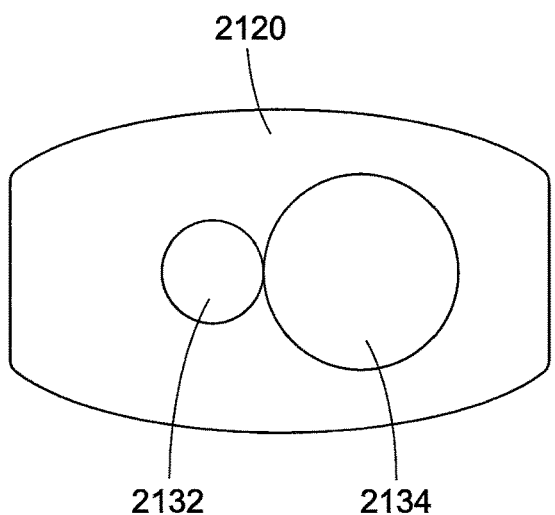

Regarding FIG. 21, it should be noted that the first compartment 2132 and the second compartment 2134 can generally take any shape. FIG. 22, FIG. 23, and FIG. 24 are top views of the closed end of an injection device and show different embodiments. In FIG. 22, the inner wall 2130 divides the volume of the barrel in half. In FIG. 23, the inner wall 2130 is bent so that the first compartment 2132 takes up about 75% of the volume of the barrel. In FIG. 24, the barrel contains two separate compartments 2132, 2134 which are joined at the bottom near the open end (not visible).

Figure 27:
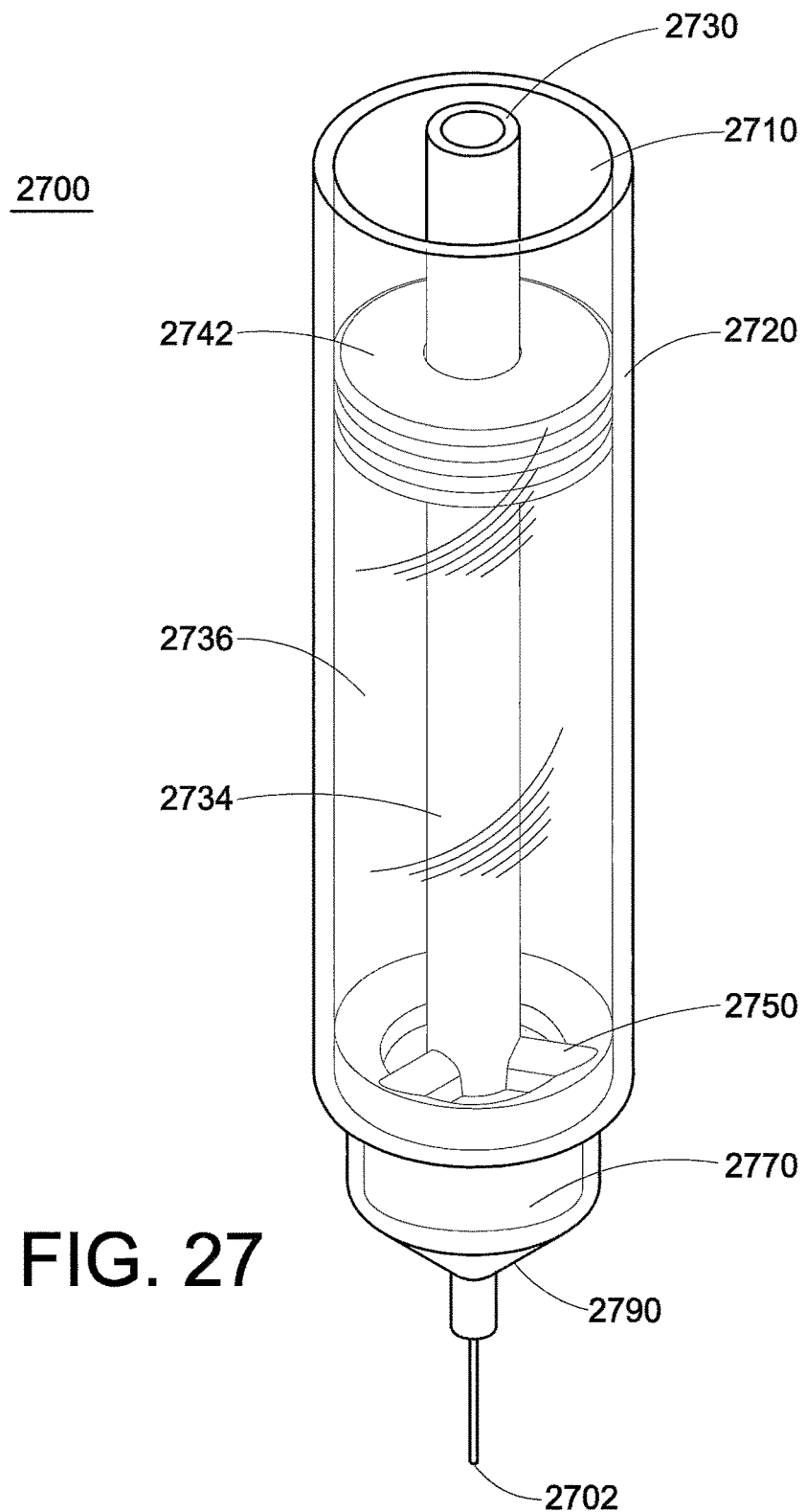
Figure 28:
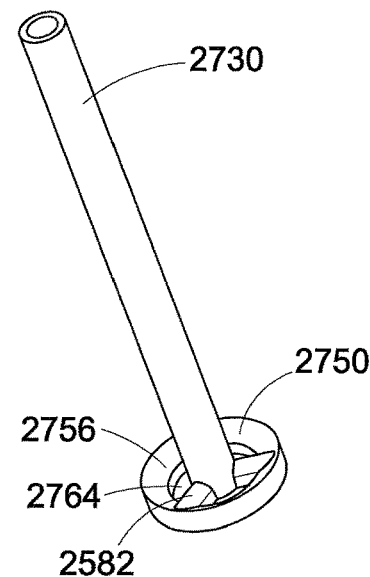
Figure 29:
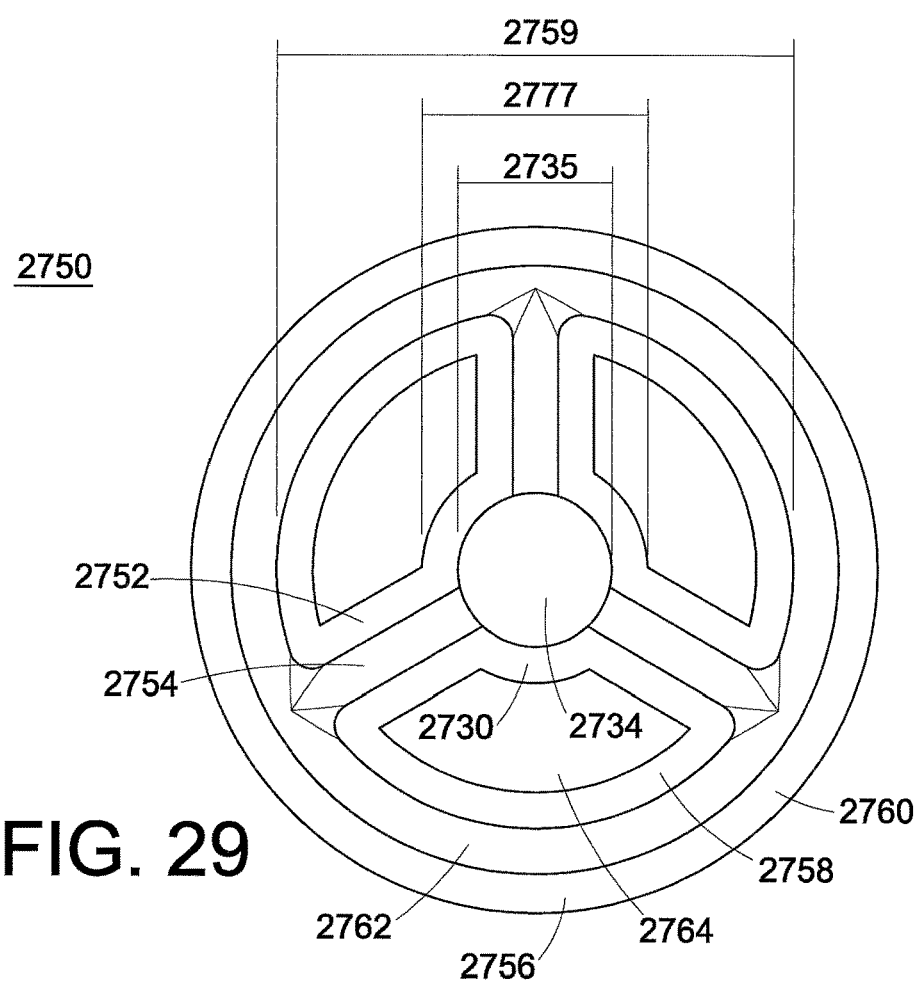
Figure 30:
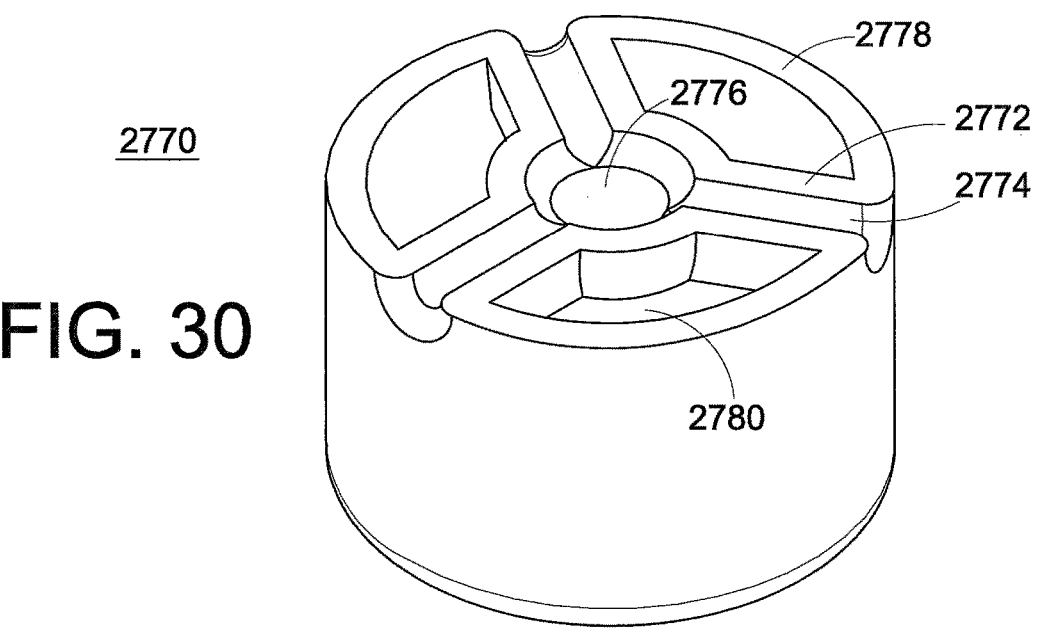
Figure 31:
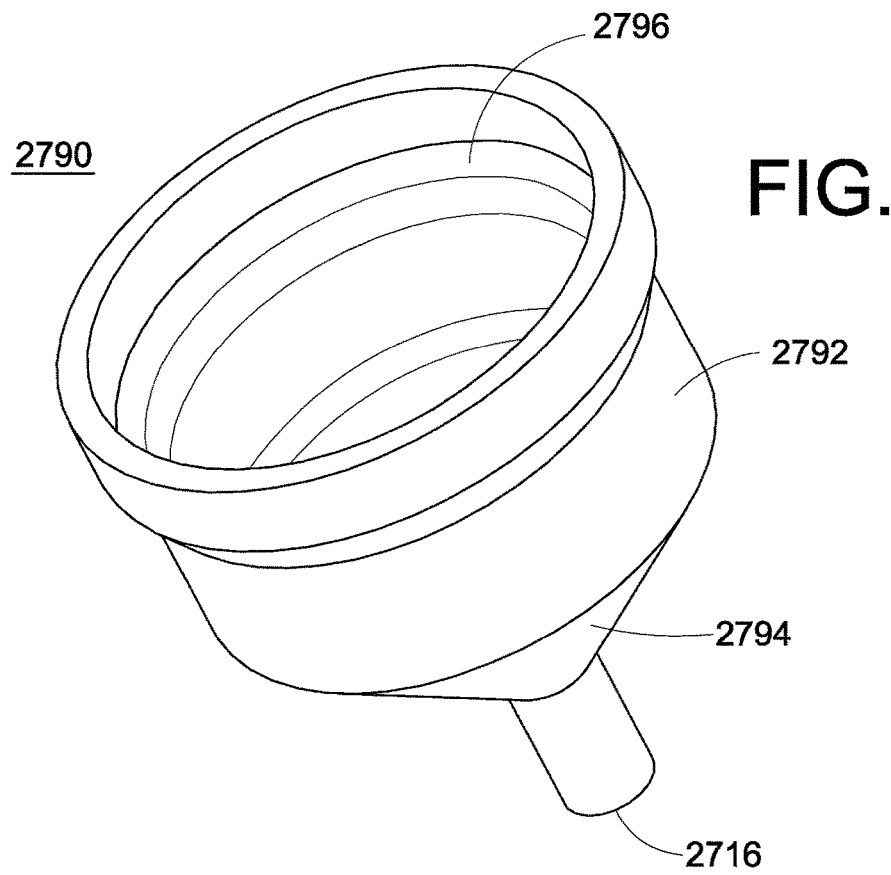
Figure 32:
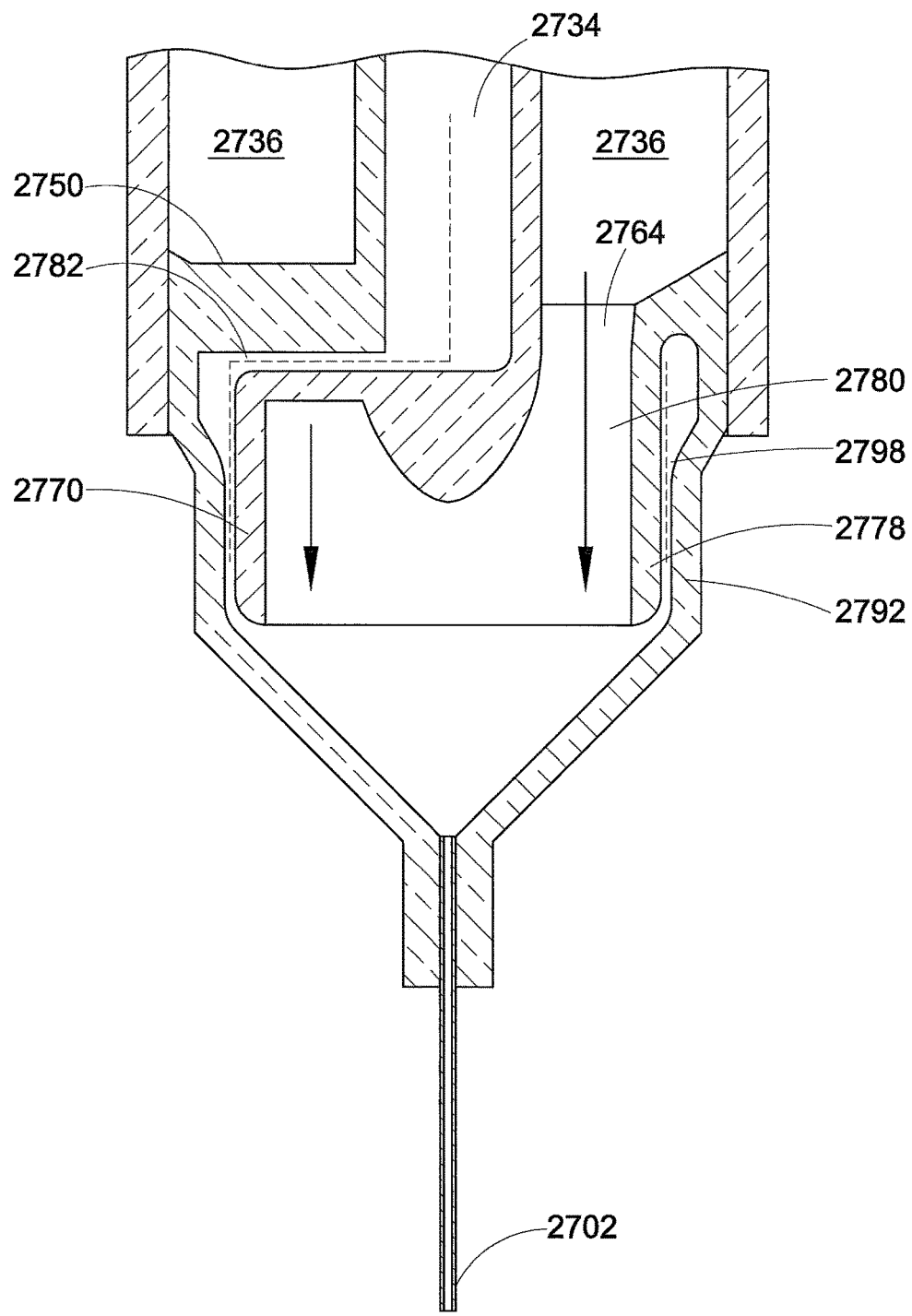

FIGS. 27-32 are various views of another exemplary embodiment of an injection device that is contemplated for core annular flow and uses flow inversion. FIG. 27 is a perspective interior view of the injection device. FIG. 28 is a perspective view of some internal components of the injection device. FIG. 29 is a bottom view of a flow cap of the injection device. FIG. 30 is a perspective view of a flow base of the injection device. FIG. 31 is a perspective view of a needle hub of the injection device. FIG. 32 is a side cross-sectional view of the injection device that shows fluid flow through the injection device.

Referring first to FIG. 27, the flow inversion injection device 2700 includes a hollow barrel 2710 which is formed from a sidewall 2720. The base of the injection device is formed from a needle hub 2790 and includes a needle 2702. It should be noted that this depiction differs from other figures previously described. The needle hub 2790 of the injection device can either be made separately from the sidewall 2720, or they can be made as one integral component. An inner concentric wall 2730 is located within the barrel 2710. An inner compartment 2734 and an outer compartment 2736 within the barrel are defined by the inner concentric wall. Located beneath the inner concentric wall is a flow cap 2750 and a flow base 2770. The plunger is similar to that depicted in FIG. 10 or FIG. 11, with a central piston located within the inner compartment (not depicted) and a ring piston 2742 in the outer compartment. The two pistons are connected to a common shaft (not depicted) and will travel simultaneously at the same rate through the barrel.

Referring now to FIG. 28, the inner concentric wall 2730 and the flow cap 2750 are usually made as one integral piece. The inner concentric wall is at the center of the flow cap. Spokes 2582 extend from the inner concentric wall to an annular ring 2756. Throughbores 2764 are formed between the center of the flow cap and the annular ring 2756. Three spokes are depicted here, though this number may vary as desired.

FIG. 29 is a bottom view of the flow cap 2750. The inner concentric wall 2730 is at the center of the flow cap. Each spoke 2752 has a radial groove 2754 which extends from the center of the flow cap. A circumferential groove 2762 is present on the underside of the annular ring. The radial grooves 2754 join the inner compartment 2734 of the injection device to the circumferential groove 2762. The annular ring 2756 includes an inner ring wall 2758 and an outer ring wall 2760 which are separated by the circumferential groove 2762. Throughbores 2764 are present between the inner concentric wall 2730 and the inner ring wall 2758, and fluid in the outer compartment will flow through the throughbores.

FIG. 30 is a perspective view of a topside of the flow base 2770. The flow base includes a central surface 2776 with spokes 2772 extending to an annular wall 2778. It should be noted that the annular wall has a height which is greater than that of the central surface. Each spoke 2772 includes a radial groove 2774 which extends to and through the annular wall 2778. Throughbores 2780 are also present in the flow base 2770 between the annular wall 2778 and the central surface 2776.

Referring back to FIG. 29, the inner compartment has an inner diameter 2735 equal to the internal diameter of the inner concentric wall 2730. The central surface 2776 of the flow base has a diameter 2777 equal to the diameter of the outer diameter of the inner concentric wall. The radial spokes of the flow cap are aligned with the radial spokes of the flow base. Similarly, the throughbores of the flow cap are aligned with the throughbores of the flow base. The annular wall 2778 of the flow base has an outer diameter which is equal to the outer diameter 2759 of the inner ring wall 2758 of the flow cap (formed by the circumferential groove 2762).

FIG. 31 is a perspective view of the needle hub 2790. The needle hub 2790 is formed from a sidewall 2792 and a conical wall 2794 that tapers to form an orifice 2716 through which fluid will pass. The flow base will be seated within the needle hub. The flow cap will rest upon a horizontal stop surface 2796 within the needle hub, or upon the needle hub itself.

The low-viscosity annular fluid is placed in the inner compartment 2734, while the high-viscosity core fluid is located in the outer compartment 2736.

FIG. 32 illustrates how the core fluid and the annular fluid reverse their orientation as they pass through a flow diverter formed by the flow cap 2750 and the flow base 2770. The flow cap 2750 and the flow base 2770 cooperate together so that each radial spoke forms a tunnel through which fluid in the inner compartment 2734 is channeled to the circumferential groove 2762. There is an annular gap 2798 between the needle hub sidewall 2792 and the annular wall 2778 of the flow base 2770. When the plunger (not depicted) is depressed, low-viscosity fluid can flow from the inner compartment 2734 through the tunnel 2782 formed in the radial spokes to the annular gap 2798, and subsequently in an annular form through the needle 2702. This flow is illustrated in dotted line. The high-viscosity fluid in the outer compartment 2736 flows directly downwards through the throughbores 2764, 2780 of the flow diverter into the center of the needle. This flow is illustrated in solid line. Core annular flow is thus created. The term "flow inversion" refers to the low-viscosity fluid being stored in the "core" (i.e. the inner compartment) but subsequently flowing in the annulus, and the high-viscosity fluid being stored in the annular but subsequently flowing in the core.

Figure 33:
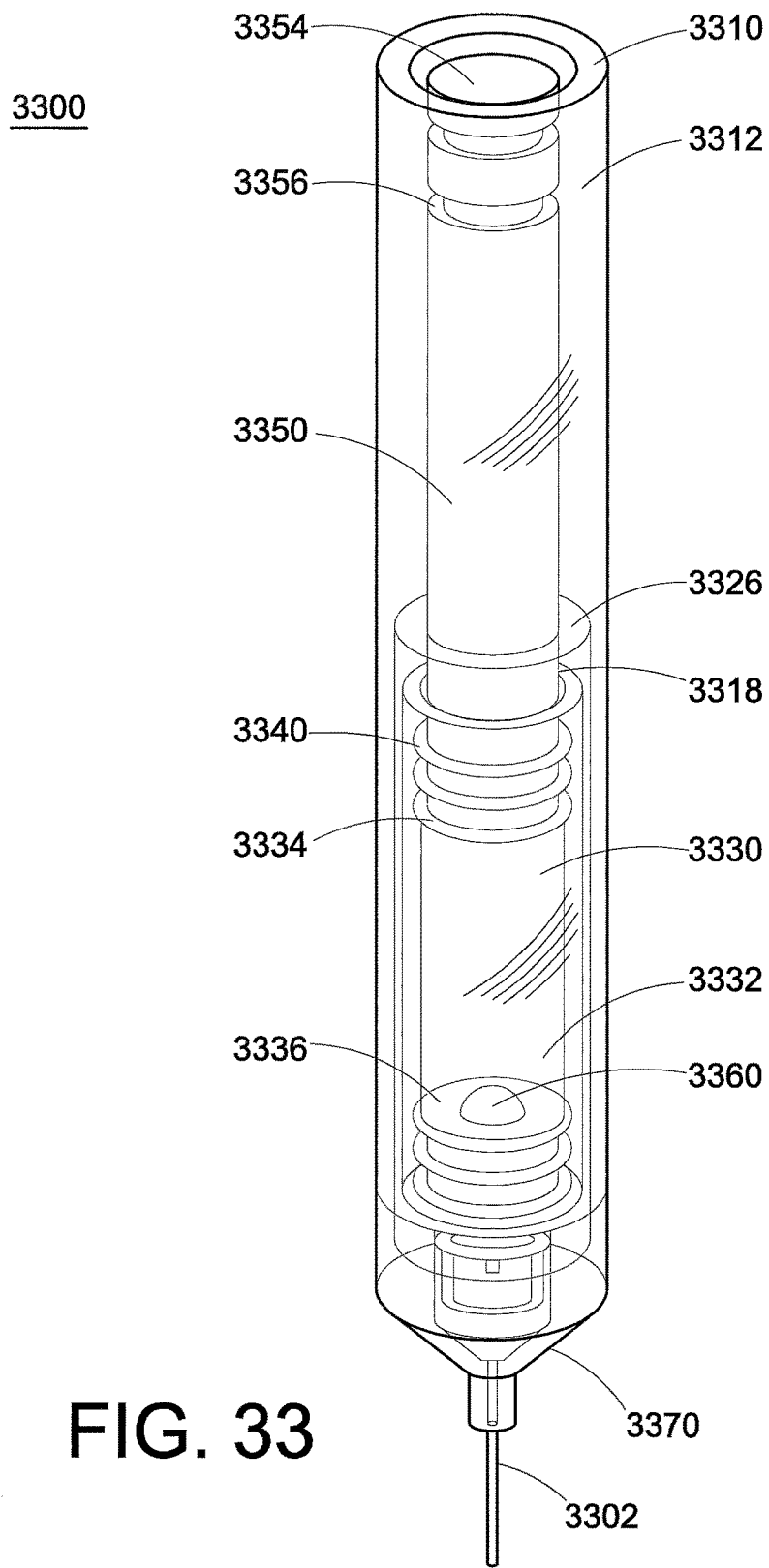
Figure 34:
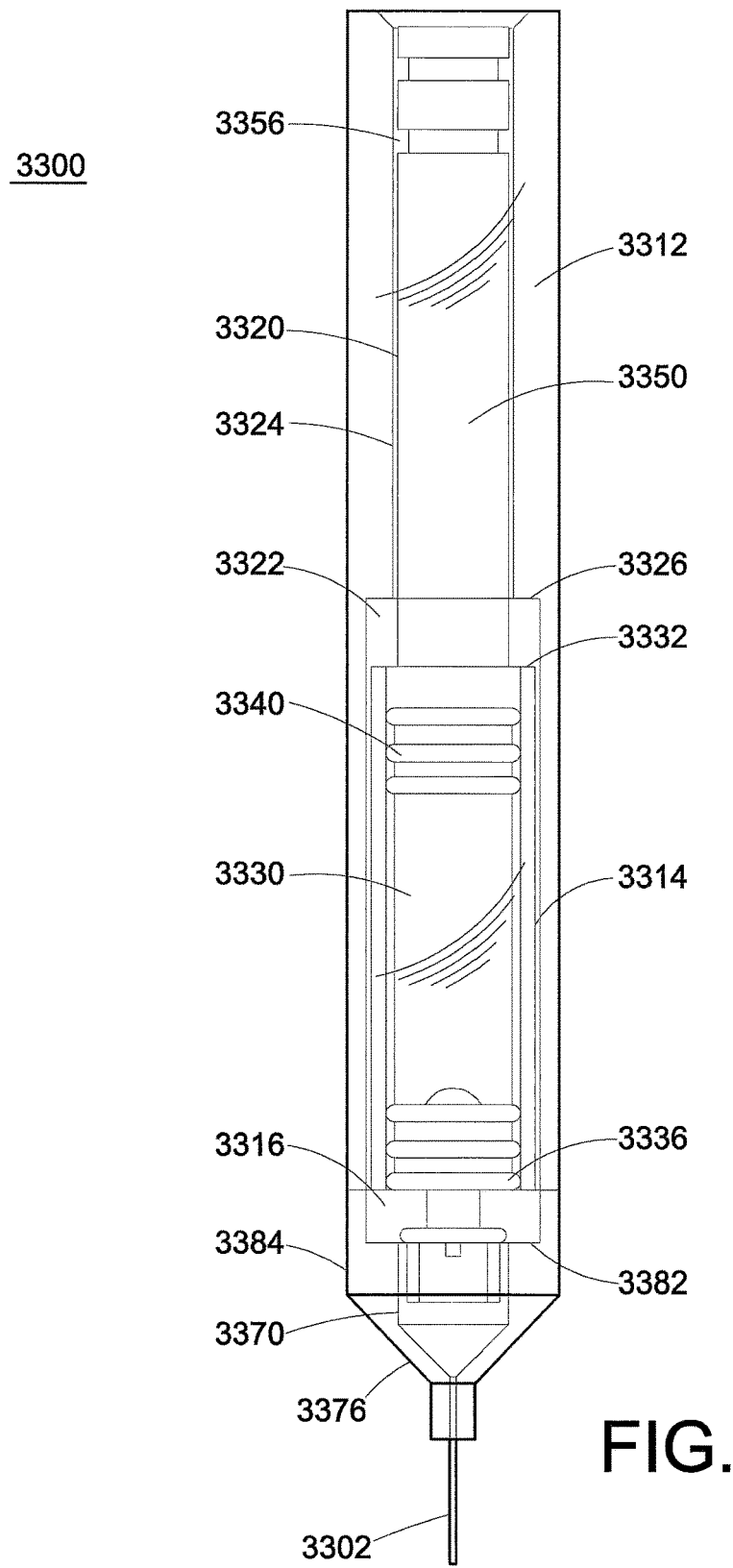

FIGS. 33-40 are various views of another exemplary embodiment. This injection device can be described as a "stacked" syringe, in which the low-viscosity fluid is stored above the high-viscosity fluid inside the barrel. FIG. 33 is a perspective view of the internal components of the injection device. FIG. 34 is a side view of the internal components of the injection device. FIG. 35 is a side cross-sectional view of the internal components of the injection device. FIG. 36 is a plan cross-sectional view showing the diameters of various internal components of the injection device. FIG. 37 is a view of the plunger rod of the injection device. FIG. 38 is a view of the core container of the injection device. FIG. 39 is a view of the pin which is located within the base of the injection device. FIG. 40 is a view of the needle hub.

Referring first to FIGS. 33-35, the injection device 3300 includes a barrel 3310 which is formed from a sidewall 3312. A needle hub 3370 is located at the base of the sidewall, and a needle 3302 is connected to the needle hub. A hollow pin 3360 sits upon and is coaxial with the needle hub 3370. The barrel sidewall 3312 and the needle hub 3370 are shaped to form a lower volume 3318, which runs for approximately half the height of the sidewall. An upper wall 3326 of the barrel sidewall marks the upper end of the lower volume 3318. Located within the lower volume 3318 is a core container 3330. The core container 3330 is formed from a sidewall 3332, a floor 3336 with a central hole through which the hollow pin 3360 can pass, and a core plunger 3340 at the top of the sidewall. The core plunger 3340 initially cooperates with grooves 3334 located at the top of the core container sidewall 3332, but with the application of sufficient force can be dislodged from the grooves. A plunger rod 3350 is inserted into the barrel and contacts the core plunger 3340. The upper end 3354 of the plunger rod includes seals 3356 which prevent fluid from leaking out of the barrel.

Referring to FIG. 34, the lower volume 3318 is more easily visualized. The needle hub 3370 includes an internal surface 3382 upon which the hollow pin sits. The needle hub also includes a sidewall 3384 and a conical wall 3376 that form exterior surfaces. The floor 3336 of the core container is spaced apart from the internal surface 3382, forming a lower space 3316 in which low-viscosity fluid can be contained. The upper wall 3326 of the barrel sidewall is spaced apart from the top of the sidewall 3332 of the core container, forming an upper space 3322 in which low-viscosity fluid is also contained. The outer diameter of the core container is less than the inner diameter of the lower volume, so that the upper space 3322 and lower space 3316 are joined together by a lower annular space 3314. The diameter of the plunger rod 3350 is less than the inner diameter of the barrel sidewall 3312 in the upper volume above the lower volume, forming an upper annular space 3320 in which low-viscosity fluid is contained.

Referring now to FIG. 35, this cross-sectional view permits easier visualization of the paths through which fluid will flow. The needle hub 3370 contains an internal cylindrical wall 3378 which defines an internal passage 3380 and an annular passage 3372 surrounding the internal passage. These passages are located below the internal surface 3382, and permit fluid to flow from one side to the other and to the needle 3302. The hollow pin 3360 is located above the internal passage 3380. Side ports 3366 are located at an upper tip 3364 of the hollow pin, and are initially covered by the floor 3336 of the core container. High-viscosity fluid is contained within the core container 3330. Low-viscosity fluid is contained in the lower space 3316, the lower annular space 3314, the upper space 3322, and the upper annular space 3320. These four locations together may be considered to form an annular compartment that contains the low-viscosity fluid. The annular compartment can also be considered to be defined by the barrel sidewall 3312, the plunger rod 3350, the core container 3330, and the needle hub 3370. A series of slits (not visible) in the horizontal surface of the needle hub joins the lower space 3316 to the annular passage 3372.

FIG. 36 is a plan cross-sectional view illustrating the various diameters involved. The barrel sidewall has an outer diameter 3311. The barrel sidewall has an inner diameter 3313 in the lower volume. The core container sidewall has an outer diameter 3331 and an inner diameter 3333. The barrel sidewall has an inner diameter 3315 in the upper volume. Finally, the plunger rod has a diameter 3355. The lower annular space 3314 containing low-viscosity fluid is the space between the barrel sidewall lower volume inner diameter 3313 and the core container sidewall outer diameter 3331. The upper annular space 3320 containing low-viscosity fluid is the space between the barrel sidewall upper volume inner diameter 3315 and the plunger rod diameter 3355.

FIG. 37 is a view of the plunger rod 3350 of the injection device. The upper end 3354 of the shaft 3352 includes seals 3356, typically o-rings, for sealing the barrel.

FIG. 38 is a view of the core container 3330 of the injection device. The sidewall 3332 is visible, and forms a tube. The floor 3336 of the core container can be formed from any type of sealing means. A central hole 3338 is present in the floor, through which the hollow pin will pass. Grooves 3334 are located at the top of the sidewall. The circumference of the core plunger 3340 interacts with the grooves. It should be noted that the core plunger can be made separately from the plunger rod, or could be integral to the plunger rod. It should be noted that the floor 3336 of the core container is fixed in place, whereas the core plunger 3340 can move up and down within the core container 3330 with the application of sufficient force. A central hole 3342 may also be present in the core plunger, if desired.

FIG. 39 is a view of the hollow pin. The hollow pin 3360 is made from a tubular wall 3362 that is sealed at the upper tip 3364. The upper tip includes side ports 3366 which fluidly connect the upper surface of the pin to the lower surface. A flange 3368 extends radially from the base of the tubular wall, and is used to seat the pin. As seen in FIG. 35, the floor 3336 of the core container covers the side ports 3366, preventing fluid flow through the hollow pin when the plunger is not depressed.

FIG. 40 is a view of the needle hub 3370. The needle hub is formed from a sidewall 3384 and a conical wall 3376, with the conical wall tapering to form an orifice 3306 through which fluid can flow. The needle hub includes an internal surface 3382 within the sidewall. The internal surface includes a central hole 3374 which is aligned with the tubular portion of the hollow pin. The internal surface 3382 also includes slits 3386 spaced apart from the central hole 3374. Referring again to FIG. 35, the central hole 3374 feeds the internal passage 3380, while the slits 3386 feed the annular passage 3372 beneath the internal surface.

Turning back now to FIG. 35, fluid flow begins when the plunger rod 3350 is depressed. Initially, due to the joinder of the plunger rod 3350 with the core container 3330 through the core plunger 3340, the core container also travels downwards towards the flange 3368 of the hollow pin. As the core container travels downwards, the lower space 3316 decreases in volume. The low-viscosity fluid present in the lower space flows through the slits 3386 into the annular passage 3372 and into the needle 3302. As the plunger rod 3350 and the core container 3330 travel downwards, the upper space 3322 increases in volume and the upper annular space 3320 decreases in volume. The low-viscosity fluid in the upper annular space 3320 is pushed downwards by the seals 3356 at the top of the plunger rod into the upper space 3322. Low-viscosity fluid also travels from the upper volume 3324 through the lower annular space 3314 around the core container 3330 into the lower space 3316. The core container 3330 finally stops atop the flange 3368 of the hollow pin. At this point, the side ports 3366 of the hollow pin are exposed. As the plunger rod 3350 continues to be depressed, the force eventually disengages the core plunger 3340 from the grooves at the top of the core container sidewall 3332. The core plunger then pushes high-viscosity fluid through the side ports 3366 and down the internal passage 3380 of the needle hub. The seals at the top of the plunger rod continue to push low-viscosity fluid from the upper space 3322 down around the core container and through the annular passage 3372 of the needle hub. This creates the core annular flow. The core plunger 3340 can be depressed until it contacts the floor 3336 and the hollow pin 3360 enters the central hole 3342 in the core plunger. The seals 3356 of the plunger rod should remain above the upper space 3322 of the barrel.

Materials for making the various components of the different injection devices disclosed herein are known in the art, as are methods for making such injection devices.

The processes and devices described herein may be used to deliver as part of the high-viscosity fluid, protein microparticles made using the processes described in U.S. Provisional Patent Application Ser. No. 61/556,047, filed Nov. 4, 2011, the disclosure of which is hereby incorporated by reference in its entirety. They can also be used as part of the systems described in U.S. Provisional Patent Application Ser. No. 61/556,542, filed Nov. 4, 2011, or in the devices described in U.S. Provisional Patent Application Ser. No. 61/556,709, filed Nov. 4, 2011, the disclosures of which are hereby incorporated by reference in their entirety.

The following examples are for purposes of further illustrating the present disclosure. The examples are merely illustrative and are not intended to limit processes or devices made in accordance with the disclosure to the materials, conditions, or process parameters set forth therein.

Example 1

Rheological constitutive models describing the relationship between protein concentration and viscosity were constructed to assess the magnitude of concentrations which might be delivered with core annular flow. It was assumed that the maximum allowable forces for an auto-injector and a manual syringe were 10 newtons and 20 newtons, respectively. Two potential low viscosity annular fluids, perfluorohexane (1.1 cP) and perfluorooctyl bromide (0.9 cP), were modeled in the annular region. The maximum concentration of protein in the core region was then calculated for a given viscosity. As a baseline, a lubricant having a viscosity of 10 cP was modeled in the annular region. The results are shown in FIG. 7. The top two lines are accomplished with manual injection, the next two lines are done with an auto-injector, and the bottommost line (circles) is for manual injection. As seen here, it is possible to deliver a protein solution at a concentration of more than 450 mg/mL and having a viscosity of up to 1000 cP using a manual syringe with an injection force of 20N.

Example 2

Experiments were performed to measure the pressure drop during delivery of a viscous fluid with core annular flow.

Two high-viscosity fluids were prepared. The first high-viscosity fluid was an aqueous solution of xanthan gum. The xanthan gum was mixed into water at 0.15 weight percent and had an absolute viscosity of 88 cP at 10/s (i.e. 10 Hz). This solution decreased in viscosity with increasing shear rate following a power law curve ($n=0.39$ and $m=357$). The core fraction occupied by the xanthan gum during flow experiments was 0.63. The second high-viscosity fluid was an aqueous solution of bovine serum albumin (BSA). BSA was mixed into phosphate buffered saline (PBS) at a concentration of 200 mg/mL and had an absolute viscosity of 10.3 cP at 10/s. This solution decreased in viscosity with increased shear rate following a power law curve ($n=0.21$ and $m=18$). The core fraction occupied by the BSA solution during flow experiments was 0.63. The low-viscosity fluid used in the annular region was water.

The high-viscosity fluids and the water were run through a slit flow apparatus. The apparatus provided a rectangular cross section. The apparatus is depicted in FIG. 8. Briefly, the apparatus 800 included a Y-shaped channel. A core fluid inlet 810 flowed directly into the stem 802, while the annular fluid flowed from an annular fluid inlet 820 through the arms 804 and then into the stem 802. Through the stem, core annular flow was present. The fluids then flowed through an outlet 830 that was located at the bottom of the stem of the Y.

The pressure drop was measured with a glass capillary manometer for various flow rates. For comparison, experiments were also performed where only the high-viscosity fluid was run through the slit flow apparatus, i.e. no low-viscosity lubricant was provided.

Figure 9:
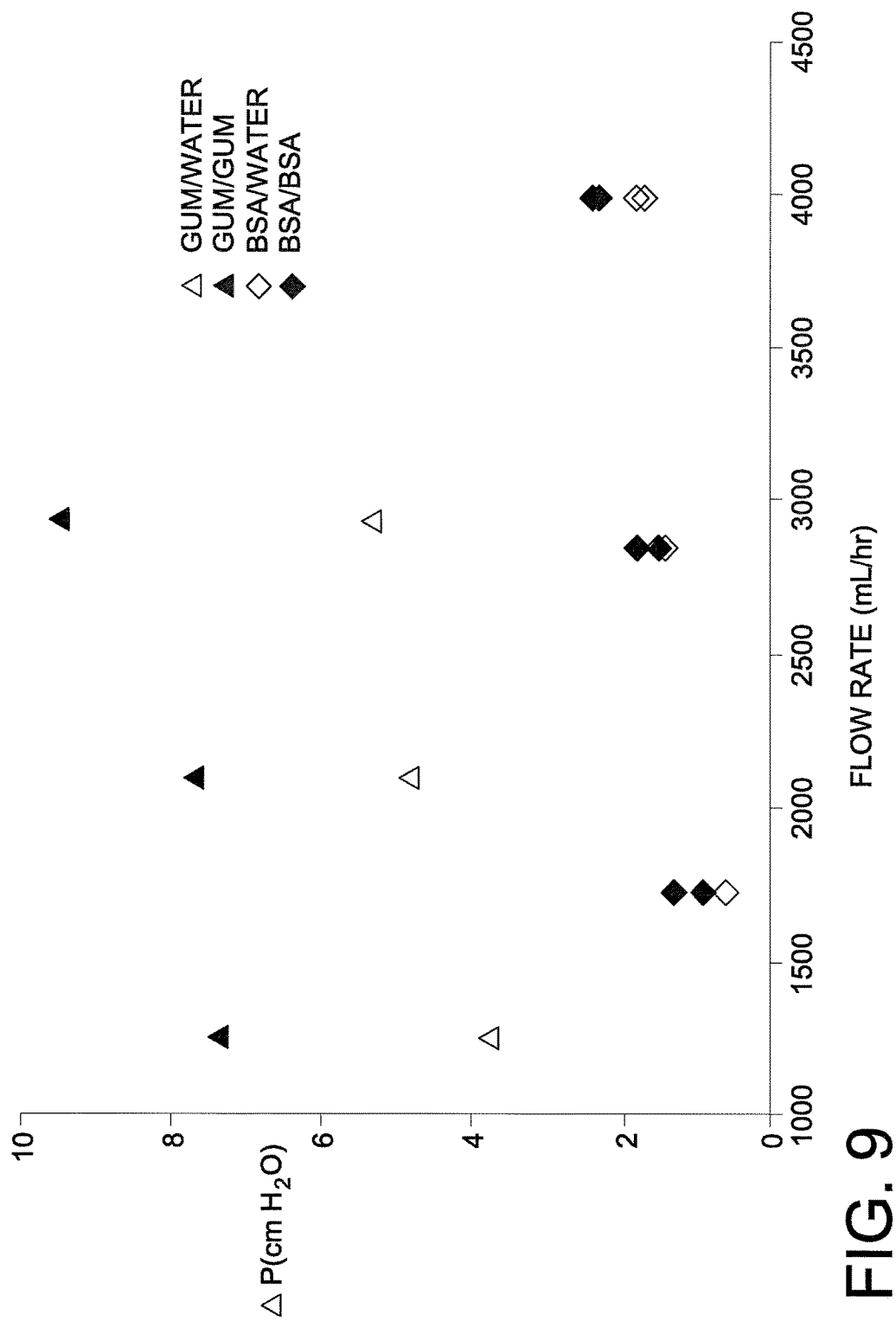

The results are shown in FIG. 9. The labels here are marked as "core fluid/annular fluid". The examples where the core fluid and annular fluid are the same did not show core annular flow. As seen here, when comparing Gum/Water to Gum/Gum, the Gum/Water results showed a lower pressure drop. Similarly, when comparing BSA/Water to BSA/BSA, the BSA/Water results showed a lower pressure drop. The Gum/Water and BSA/Water results used water as a low-viscosity fluid in the annular region, and the lower pressure drop reflects the fact that core annular flow effectively reduces the pressure required for delivery of the viscous fluid at a given flow rate.

Example 3

Figure 25:
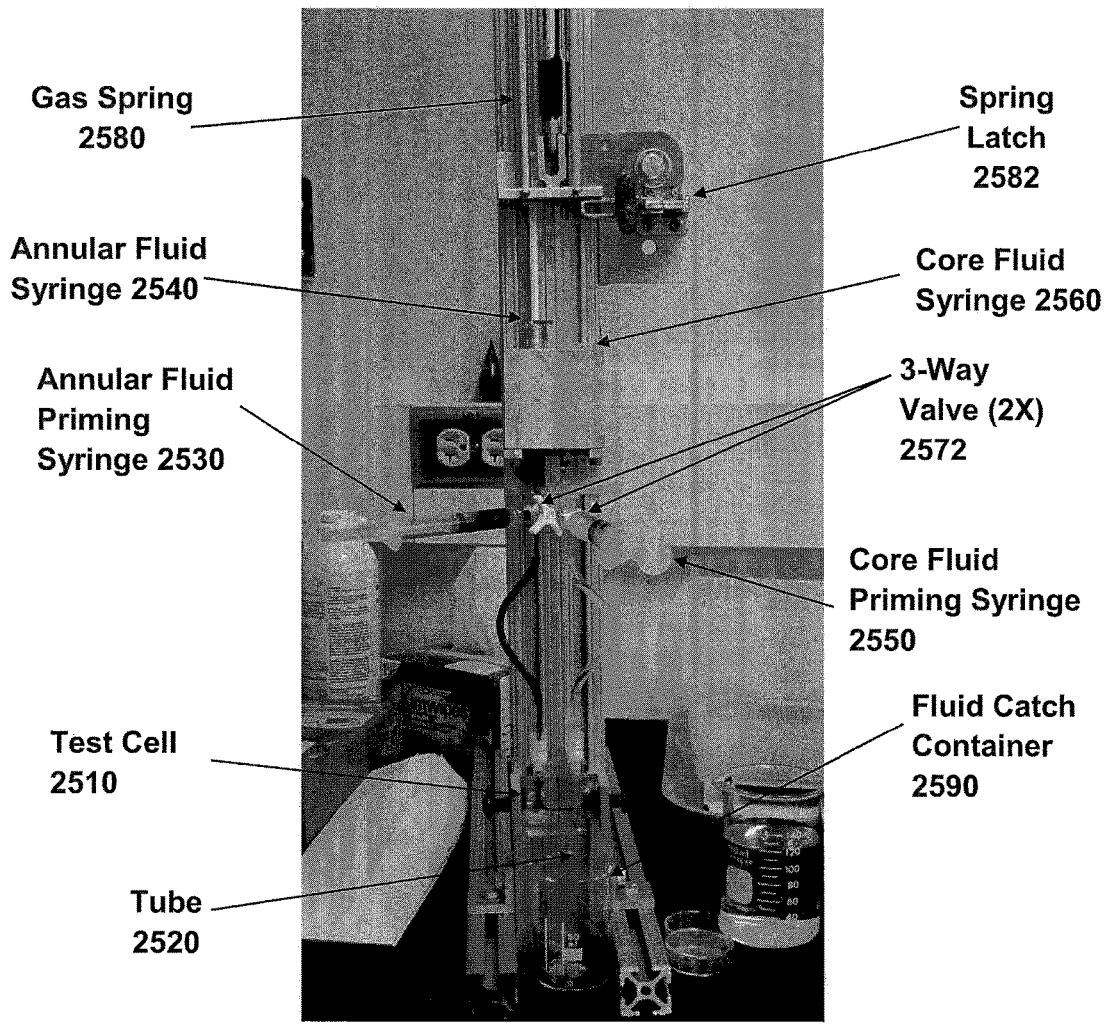

A test stand was made as seen in FIG. 25 for proof of concept. The setup included a test cell 2510, a half-inch tube 2520, an annular fluid priming syringe 2530, an annular fluid syringe 2540, a core fluid priming syringe 2550, a core fluid syringe 2560, two 3-way valves 2572, a gas spring 2580, a spring latch 2582, and a fluid catch container 2590.

Figure 26:
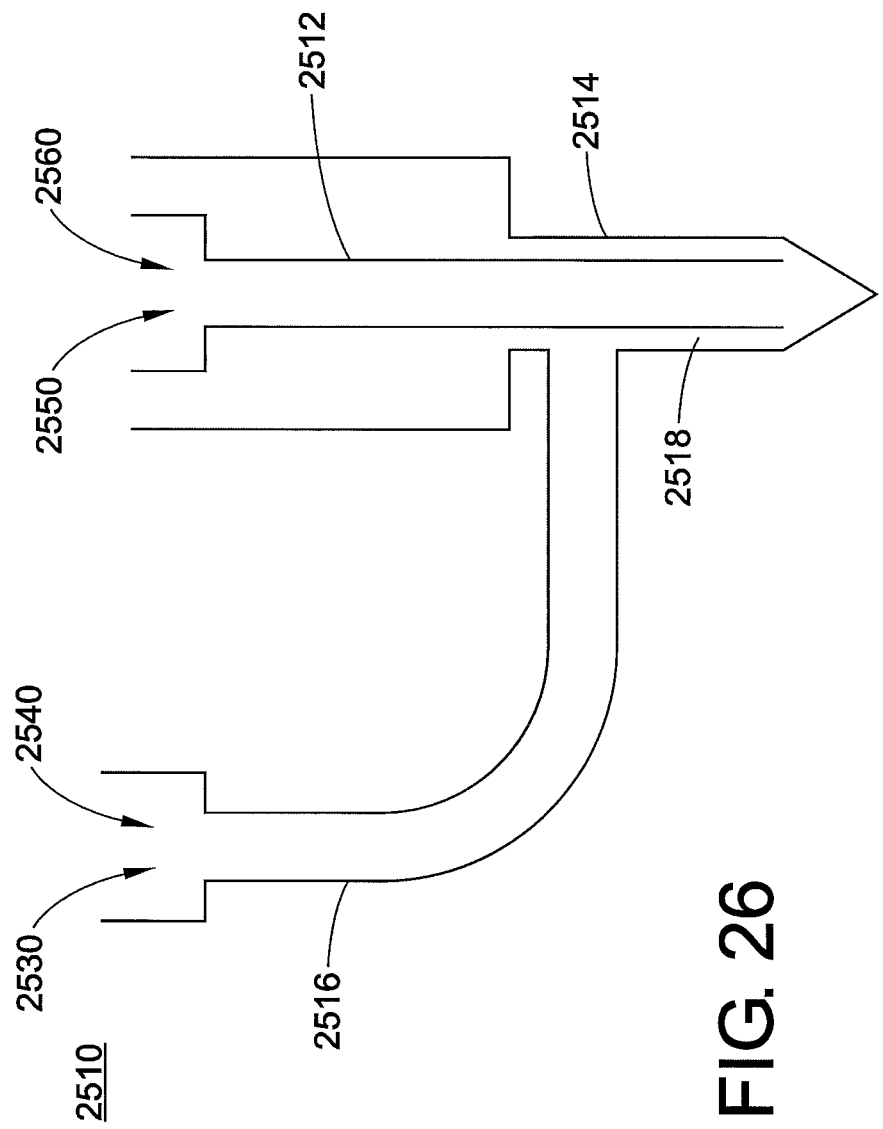

FIG. 26 is a magnified side view of the test cell 2510, where the annular fluid and the core fluid were combined. The test cell here was designed for a 75/25 core to annulus volumetric flow ratio. In this regard, the right side of the test cell included an inner concentric wall 2512 and an outer wall 2514. The inner wall formed a straight vertical pipe through which the core fluid flowed straight down. An annulus 2518 was created between the inner wall and the outer wall. The annular fluid entered from the left side 2516 of the test cell. The inner wall ended where the outer wall began to constrict at a 30° angle, and the two fluids met at the constriction. The triangular shape of the annulus 2518 illustrates the nipple that would go to a needle.

Based on this design, a 3 mL plastic Becton-Dickinson (BD) syringe was used for the core fluid syringe. A 1 mL BD syringe was used for the annular fluid syringe. A 5 lbf gas spring with a 2" stroke was used to drive both fluid syringes simultaneously. A latch held the gas spring in the retracted position until a test was run. Two 3-way valves and priming syringes were used to prime both the fluid syringes and the rest of the test cell between runs. At the bottom of the fixture was the test cell which combined the core and annular flows and directed them through a 27 G half-inch-long stainless steel tube and into the fluid catch container.

Each test run was performed using the following procedure: The gas spring was retracted and the latch was set. Using the 3-way valve and the core priming syringe, the core fluid syringe was filled with 1 mL of core fluid. Using the 3-way valve and the annular priming syringe, the annular fluid syringe was filled with 0.4 mL of annular fluid. Using the 3-way valve and the core priming syringe, the tubing and test cell was primed with core fluid. Using the 3-way valve and the annular priming syringe, the tubing and test cell was primed with annular fluid. Both 3-way valves were set to allow the fluid syringes to open to the test cell and to close off the priming syringes. The latch was then released to initiate the run, pushing the annular fluid and the core fluid with the same force, and the time was recorded to deliver the fluids. Syringes were used for 10 or less consecutive runs with the same fluid, due to friction problems attributed to silicone lubricant on the plunger wearing off.

Two different fluids were used. The high-viscosity fluid was a glyercol/water solution with a viscosity of 85 centipoise (cP). The low-viscosity fluid was distilled water, with a viscosity of 1 cP. Viscosity was measured using a TA Ar2000ex rheometer, a 0.5° 20 mm steel cone, Peltier temperature stabilization, at 23° C. with two minutes equilibration time.

Four different sets of experiments were run. First, water was used as both the core fluid and the annular fluid. Second, glycerol was used as both the core fluid and the annular fluid. Third, glycerol was used as the core fluid and water was used as the annular fluid. Fourth, to show that the combination of water and glycerol is achieving core annular flow rather than merely reducing the total viscosity by combining, the resultant solution from the third set was used as both the core fluid and the annular fluid. The resultant solution had a viscosity of 17 cP.

The time was recorded by watching when fluid had completely exited the test cell and entered the catch container. However, when running glycerol for both the core and annular fluids, it was difficult to determine exactly when the fluid had completed delivery. As a result, a note was taken when the plungers of both fluid syringes bottomed out for a conservative estimate.

The results are shown in Table 1. The two fluids are listed in core/annular.

TABLE 1

|  | Water/Water (sec) | Glycerol/Glycerol (sec) | Glycerol/Water (sec) | Resultant/Resultant (sec) |
| --- | --- | --- | --- | --- |
| Run 1 | 4 | 180 | 6 | 21 |
| Run 2 | 3 | 176 | 5 | 23 |
| Run 3 | 4 | 188 | 6 | 20 |
| Run 4 | 4 | 182 | 6 | N/A |
| Run 5 | 4 | 174 | 6 | N/A |
| Run 6 | 4 | N/A | 8 | N/A |
| Run 7 | 4 | N/A | N/A | N/A |
| Average | 4 | 180 | 6 | 21 |

The conservative estimate for the glycerol/glycerol run was 85 seconds. The core-annular flow provided a 93% reduction in delivery time when compared to this conservative estimate. In contrast, simply reducing the viscosity of the core fluid by mixing in the volume of annular fluid (i.e. the resultant) resulted in only a 75% reduction in delivery time. While these values depend on the two fluids used and their properties, the test clearly showed that core-annular behavior was occurring and demonstrated a significant increase in performance of the system.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An injection device for creating core annular flow, comprising:

a barrel having an interior space formed from a sidewall, an open end having an orifice, and an inner concentric wall within the sidewall, wherein the inner concentric wall divides the interior space into an inner compartment and an outer compartment;

a flow diverter located between the inner compartment and the orifice; and a plunger operating within the barrel;

wherein the flow diverter is adapted so that depressing the plunger causes fluid in the inner compartment to form an annulus and causes fluid in the outer compartment to flow as a core surrounded by the annulus.

2. The injection device of claim 1, wherein the flow diverter is formed from a flow cap and a flow base;

wherein a center of the flow cap connects to the inner concentric wall, and at least one radial spoke extends from the center of the flow cap to an annular ring, an underside of the annular ring including a circumferential groove, the circumferential groove creating an inner ring wall and an outer ring wall;

wherein the flow base includes a central surface with at least one radial spoke extending from the central surface to an annular wall;

wherein the at least one radial spoke of the flow cap and the at least one radial spoke of the flow base cooperate to form a tunnel that channels fluid from the inner compartment to the circumferential groove.

3. The injection device of claim 2, wherein the central surface of the flow base has a diameter equal to an outer diameter of the inner concentric wall.

4. The injection device of claim 2, wherein the annular wall of the flow base has an outer diameter equal to the outer diameter of the inner ring wall of the flow cap.

5. The injection device of claim 2, wherein the inner concentric wall and the flow cap are formed as one integral component.

6. The injection device of claim 2, wherein the flow cap includes throughbores between the inner concentric wall and the inner ring wall; and wherein the flow base includes throughbores between the central surface and the annular wall.

7. The injection device of claim 2, wherein the flow cap rests upon a horizontal stop surface within a needle hub, and the flow base is seated within the needle hub.

8. The injection device of claim 2, wherein the plunger comprises a central piston located within the inner compartment and a ring piston located within the outer compartment, the central piston and the ring piston being connected to a common shaft.

9. An injection device for delivering a high-viscosity fluid, comprising:

a barrel having an orifice, an interior space that is separated into a first compartment and a second compartment, and at least one channel connecting the second compartment to the first compartment, the channel being shaped so that a low-viscosity fluid flows from the second compartment circumferentially against a sidewall of the first compartment to create core annular flow;

wherein the first compartment contains the high-viscosity fluid;

wherein the second compartment contains a low-viscosity fluid; and a plunger operating within the barrel.

10. The injection device of claim 9, wherein the barrel is an outer barrel containing the first compartment, and further comprising an inner barrel that slides within the outer barrel, the inner barrel containing the second compartment.

* * * * *